United States Patent
Yu et al.

(10) Patent No.: US 12,338,284 B2
(45) Date of Patent: *Jun. 24, 2025

(54) BINDER AGAINST PROGRAMMED DEATH-LIGAND AND APPLICATION THEREOF

(71) Applicant: HUABO BIOPHARM (SHANGHAI) CO., LTD., Shanghai (CN)

(72) Inventors: Haijia Yu, Shanghai (CN); Ling Yu, Shanghai (CN); Mingqing Cai, Shanghai (CN); Xiangyang Zhu, Shanghai (CN)

(73) Assignee: HUABO BIOPHARM (SHANGHAI) CO., LTD., Shanghai (CN)

( * ) Notice: Subject to any disclaimer, the term of this patent is extended or adjusted under 35 U.S.C. 154(b) by 1001 days.

This patent is subject to a terminal disclaimer.

(21) Appl. No.: 17/424,964

(22) PCT Filed: Mar. 10, 2020

(86) PCT No.: PCT/CN2020/078596
§ 371 (c)(1),
(2) Date: Jul. 22, 2021

(87) PCT Pub. No.: WO2020/199860
PCT Pub. Date: Oct. 8, 2020

(65) Prior Publication Data
US 2022/0089741 A1    Mar. 24, 2022

(30) Foreign Application Priority Data
Apr. 1, 2019 (CN) .......................... 201910258182.5

(51) Int. Cl.
*C07K 16/28* (2006.01)

(52) U.S. Cl.
CPC ...... *C07K 16/2827* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | |
|---|---|---|
| 11,236,167 B2 | 2/2022 | Ulitin et al. |
| 2018/0186883 A1 | 7/2018 | Papadopoulos et al. |
| 2019/0077867 A1 | 3/2019 | Zhu et al. |
| 2020/0036977 A1 | 1/2020 | Kumakura et al. |
| 2022/0002418 A1* | 1/2022 | Zhu .......... C12N 15/85 |
| 2024/0010730 A1* | 1/2024 | Zhu .......... C07K 16/2827 |
| 2024/0026004 A1* | 1/2024 | Wei .......... A61K 47/68 |

FOREIGN PATENT DOCUMENTS

| | | | | |
|---|---|---|---|---|
| CN | 104749372 A * | 7/2015 | .......... | G01N 33/531 |
| CN | 105461808 A | 4/2016 | | |
| CN | 105968200 A | 9/2016 | | |
| CN | 106103482 A | 11/2016 | | |
| CN | 109929037 A | 6/2019 | | |
| WO | WO-2017205377 A2 * | 11/2017 | .......... | C07K 16/1271 |
| WO | 2018194496 A2 | 10/2018 | | |
| WO | 2018195226 A1 | 10/2018 | | |
| WO | 2019005634 A2 | 1/2019 | | |

OTHER PUBLICATIONS

Almagro & Fransson, Humanization of antibodies, Frontiers in Bioscience 2008; 13: 1619-33 (Year: 2008).*
Gura, T., Systems for Identifying New Drugs Are Often Faulty, Science, 1997, 278:1041-1042 (Year: 1997).*
Kaiser, J., First pass at cancer genoome reveals complex landscape, Science, 2006, 313:1370 (Year: 2006).*
Gerdes et al. Emerging understanding of multiscale tumor heterogeneity, Front. Oncol. Dec. 18, 2014 doi: 10.3389/fonc.2014.00366, pp. 1-12 (Year: 2014).*
International Search Report mailed May 13, 2020 corresponding to PCT/CN2020/078596 filed Mar. 10, 2020; 3 pages.
Alsaab et al., "PD-1 and PD-L1 Checkpoint Signaling Inhibition for Cancer Immunotherapy: Mechanism, Combinations, and Clinical Outcome," Frontiers in Pharmacology, Aug. 23, 2017, pp. 1-15, vol. 8, Article 561, 15 pages.
Xie et al., "Construction of an anti-programmed death-ligand 1 chimeric antigen receptor and determination of its antitumor function with transduced cells," Oncology Letters, Mar. 7, 2018, pp. 157-166, vol. 16, 10 pages.

* cited by examiner

*Primary Examiner* — Peter J Reddig
*Assistant Examiner* — Cheng Lu
(74) *Attorney, Agent, or Firm* — Mintz Levin Cohn Ferris Glovsky and Popeo, P.C.

(57) ABSTRACT

Provided is an anti-PD-L1 monoclonal antibody. The antibody can be used to prepare a drug for preventing or treating a disease related to PD-L1.

10 Claims, 1 Drawing Sheet
Specification includes a Sequence Listing.

SEQUENCE LISTING

```
<160> NUMBER OF SEQ ID NOS: 9

<210> SEQ ID NO 1
<211> LENGTH: 120
<212> TYPE: PRT
<213> ORGANISM: Artificial sequence
<220> FEATURE:
<223> OTHER INFORMATION: Heavy chain variable region of the antibody

<400> SEQUENCE: 1

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Ala Phe Thr Gly Tyr
            20                  25                  30

Thr Ile His Trp Val Lys Gln Arg Ser Gly Leu Gly Leu Glu Trp Leu
        35                  40                  45

Gly Trp Phe Tyr Pro Gly Ser Gly Thr Leu Lys Tyr Asn Glu Lys Phe
    50                  55                  60
```

```
Lys Asp Lys Ala Thr Leu Thr Ala Asp Lys Ser Ser Thr Val Tyr
 65                  70                  75                  80

Leu Glu Leu Ser Arg Leu Thr Ser Glu Asp Ser Ala Val Tyr Phe Cys
                 85                  90                  95

Ala Arg His Gly Thr Gly Thr Leu Met Ala Met Asp Tyr Trp Gly Gln
            100                 105                 110

Gly Thr Ser Val Thr Val Ser Ser
            115                 120

<210> SEQ ID NO 2
<211> LENGTH: 112
<212> TYPE: PRT
<213> ORGANISM: Artificial sequence
<220> FEATURE:
<223> OTHER INFORMATION: Light chain variable region of the antibody

<400> SEQUENCE: 2

Asp Val Val Thr Gln Thr Pro Leu Ser Leu Pro Val Ser Phe Gly
 1               5                  10                  15

Asp Gln Val Ser Ile Ser Cys Arg Ser Ser Gln Ser Leu Ala Asn Ser
                 20                  25                  30

Tyr Gly Asn Thr Tyr Leu Ser Trp Tyr Leu His Lys Pro Gly Gln Ser
             35                  40                  45

Pro Gln Leu Leu Ile Tyr Gly Ile Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Thr Ile Lys Pro Glu Asp Leu Gly Met Tyr Tyr Cys Leu Gln Gly
                 85                  90                  95

Thr His Gln Pro Pro Thr Phe Gly Gly Gly Thr Lys Leu Glu Ile Lys
            100                 105                 110

<210> SEQ ID NO 3
<211> LENGTH: 8
<212> TYPE: PRT
<213> ORGANISM: Artificial sequence
<220> FEATURE:
<223> OTHER INFORMATION: Heavy chain variable region CDR1

<400> SEQUENCE: 3

Gly Tyr Ala Phe Thr Gly Tyr Thr
 1               5

<210> SEQ ID NO 4
<211> LENGTH: 8
<212> TYPE: PRT
<213> ORGANISM: Artificial sequence
<220> FEATURE:
<223> OTHER INFORMATION: Heavy chain variable region CDR2

<400> SEQUENCE: 4

Phe Tyr Pro Gly Ser Gly Thr Leu
 1               5

<210> SEQ ID NO 5
<211> LENGTH: 13
<212> TYPE: PRT
<213> ORGANISM: Artificial sequence
<220> FEATURE:
<223> OTHER INFORMATION: Heavy chain variable region CDR3

<400> SEQUENCE: 5
```

Ala Arg His Gly Thr Gly Thr Leu Met Ala Met Asp Tyr
1               5                   10

<210> SEQ ID NO 6
<211> LENGTH: 11
<212> TYPE: PRT
<213> ORGANISM: Artificial sequence
<220> FEATURE:
<223> OTHER INFORMATION: Light chain variable region CDR1

<400> SEQUENCE: 6

Gln Ser Leu Ala Asn Ser Tyr Gly Asn Thr Tyr
1               5                   10

<210> SEQ ID NO 7
<211> LENGTH: 9
<212> TYPE: PRT
<213> ORGANISM: Artificial sequence
<220> FEATURE:
<223> OTHER INFORMATION: Light chain variable region CDR3

<400> SEQUENCE: 7

Leu Gln Gly Thr His Gln Pro Pro Thr
1               5

<210> SEQ ID NO 8
<211> LENGTH: 120
<212> TYPE: PRT
<213> ORGANISM: Artificial sequence
<220> FEATURE:
<223> OTHER INFORMATION: Heavy chain variable region of the antibody

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Gly Tyr
                20                  25                  30

Thr Ile His Trp Val Arg Gln Ala Pro Gly Gln Arg Leu Glu Trp Met
            35                  40                  45

Gly Trp Phe Tyr Pro Gly Ser Gly Thr Leu Lys Tyr Ser Glu Lys Phe
    50                  55                  60

Gln Gly Arg Val Thr Ile Thr Arg Asp Lys Ser Leu Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Thr Gly Thr Leu Met Ala Met Asp Tyr Trp Gly Gln
                100                 105                 110

Gly Thr Leu Val Thr Val Ser Ser
        115                 120

<210> SEQ ID NO 9
<211> LENGTH: 112
<212> TYPE: PRT
<213> ORGANISM: Artificial sequence
<220> FEATURE:
<223> OTHER INFORMATION: Light chain variable region of the antibody

<400> SEQUENCE: 9

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Ala Asn Ser
                20                  25                  30

-continued

```
Tyr Gly Asn Thr Tyr Leu Ser Trp Tyr Leu His Lys Pro Gly Gln Ser
        35                  40                  45

Pro Gln Leu Leu Ile Tyr Gly Ile Ser Asn Arg Phe Ser Gly Val Pro
        50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Leu Gln Gly
                85                  90                  95

Thr His Gln Pro Pro Thr Phe Gly Gln Gly Thr Lys Leu Glu Ile Lys
            100                 105                 110
```

BINDER AGAINST PROGRAMMED DEATH-LIGAND AND APPLICATION THEREOF

RELATED APPLICATION

This application is a U.S. National Stage Application under 35 U.S.C. 371 of International Patent Application No. PCT/CN2020/078596, filed on Mar. 10, 2020, which claims priority to Chinese Patent Application No. 201910258182.5, filed on Apr. 1, 2019.

REFERENCE TO SEQUENCE LISTING

This application contains a Sequence Listing, which has been filed electronically in .xml format and is hereby incorporated by reference in its entirety. Said ASCII copy, created on Apr. 1, 2019, is named P2021-1040_Sequence_Listing.txt and is 5,833 bytes in size.

TECHNICAL FIELD

The present invention relates to the field of medicine, and specifically relates to binder against programmed death-ligand (PD-L1) and application thereof.

BACKGROUND ART

Programmed death 1 (PD-1) is a member of CD28 receptor family, which includes CD28, CTLA-4, ICOS, PD-1 and BTLA. The original members of this family, CD28 and ICOS, were discovered by enhanced function of T cell proliferation after adding monoclonal antibodies (Hutloff et al. (1999), Nature 397:263-266; Hansen et al. (1980), Immunogenics 10:247-260). Two cell surface glycoprotein ligands for PD-1 have been identified as PD-L1 and PD-L2, and they have been shown to down-regulate T cell activation and cytokine secretion after binding to PD-1 (Freeman et al. (2000), J Exp Med 192:1027-34; Latchman et al. (2001), Nat Immunol 2:261-8; Cater et al. (2002), Eur J Immunol 32:634-43; Ohigashi et al. (2000), Cl in Cancer Res 11:2947-53). PD-L1 (B7-H1) and PD-L2 (B7-DC) are both B7 homologues that bind to PD-1 but do not bind to other CD28 family members (Blank et al. 2004).

Expression of PD-L1 has been found in several human cancers, including human lung cancer, ovarian cancer, colon cancer, melanoma, and various myeloma (Iwai et al. (2002), PNAS 99:12293-7; Ohigashi et al. (2000, Cl in Cancer Res 11:2947-53). Previous results show that PD-L1, which is highly expressed in tumor cells, plays an important role in the immune escape of tumor by increasing the apoptosis of T cells. Researchers found that P815 tumor cell line transfected with PD-L1 gene can resist the lysis of specific CTL in vitro, and has stronger tumorigenicity and invasiveness after being inoculated into mice. These biological characteristics can be reversed by blocking PD-L1. Mice that knocked out the PD-1 gene and blocked the PD-L1/PD-1 pathway cannot form tumors when inoculated with tumor cells (Dong et al. (2002), Nat Med 8:793-800). It has also been suggested that PD-L1 may be associated with intestinal mucosal inflammation, and that inhibition of PD-L1 prevents atrophy associated with colitis (Kanai et al. (2003), JImmunol 171:4156-63). PD-1 is an immunosuppressive receptor first expressed on activated T cells and B cells. The interaction between the receptor and its ligand has always shown a weakened T cell response in vitro and in vivo. It has been shown that blocking the interaction between PD-1 and one of its ligands, PD-L1, improves the immunity of tumor-specific $CD8^+$ T cells, therefore, can help the immune system remove tumor cells.

The PD-1/PD-L1 pathway is a well-established target for developing antibody therapies for cancer therapy. Anti-PD-1 antibodies can also be used for chronic viral infections. Memory $CD8^+$ T cells produced after acute viral infection have high function and constitute an important component of protective immunity. On the contrary, chronic infection is often characterized by different degrees of functional impairment (failure) of virus-specific T cell response, which is the main reason why the host cannot eliminate persistent pathogens.

Although functional effector T cells are initially produced in the early stage of infection, they gradually lose their function during chronic infection. Barber et al. (Barber et al., Nature 439:682-687 (2006)) showed that mice infected with the laboratory strain of LCMV developed chronic infection resulting in high levels of the virus in both blood and other tissues. These mice initially produced strong T cell responses, but eventually became infected as the depletion of T-cells. The authors found that the decrease in the number and function of effector T cells in chronically infected mice can be reversed by injecting antibodies that block the interaction between PD-1 and PD-L1.

Recently, studies have shown that PD-1 is highly expressed in T cells from HIV-infected individuals, and the expression of receptor is associated with T cell dysfunction and disease progression (D-machi et al., Nature 443:350-4 (2006); Trautmann L. et al., Nat. Med. 12:1198-202 (2006)). In both studies, blocking the ligand PD-L1 significantly increased the proliferation of HIV-specific IFNγ-producing cells in vitro.

In short, there is still a need in the art for anti-PD-L1 antibodies that can bind to PD-L1 with high affinity and can block the binding of PD-1 to PD-L1.

SUMMARY OF THE INVENTION

The object of the present invention is to provide a PD-L1 antibody with high affinity and high biological activity and application thereof. The antibody can bind to PD-L1 with high affinity and can block the binding of PD-1 to PD-L1.

Another object of the present invention is to provide a binding molecule of programmed death ligand 1 (PD-L1) and application thereof, especially the application in the treatment and/or prevention, or diagnosis of PD-L1 related diseases such as tumors.

In a first aspect of the present invention, it provides a heavy chain variable region of an antibody, wherein the heavy chain variable region comprises the following three complementarity determining regions or CDRs:
CDR1 as shown in SEQ ID NO: 3,
CDR2 as shown in SEQ ID NO: 4, and
CDR3 as shown in SEQ ID NO: 5.

In another preferred embodiment, any one of the above amino acid sequences also includes a derivative sequence that is optionally with at least one (e.g., 1-3, preferably 1-2, more preferably 1) amino acid added, deleted, modified, and/or substituted, and is capable of retaining the binding affinity to PD-L1.

In another preferred embodiment, the heavy chain variable region further comprises human FR regions or mouse FR regions.

In another preferred embodiment, the heavy chain variable region has the amino acid sequence as shown in SEQ ID NO: 1.

In another preferred embodiment, the heavy chain variable region has the amino acid sequence as shown in SEQ ID NO: 8.

In a second aspect of the present invention, it provides a heavy chain of an antibody, which has the heavy chain variable region of the first aspect of the present invention.

In another preferred embodiment, the heavy chain of the antibody further comprises a heavy chain constant region.

In another preferred embodiment, the heavy chain constant region is of human, mouse or rabbit.

In a third aspect of the present invention, it provides a light chain variable region of an antibody, wherein the light chain variable region comprises the following three complementarity determining region CDRs:

CDR1' as shown in SEQ ID NO: 6,
CDR2' with an amino acid sequence of GIS, and
CDR3' as shown in SEQ ID NO: 7.

In another preferred embodiment, any one of the above amino acid sequences also includes a derivative sequence that is optionally with at least one (e.g., 1-3, preferably 1-2, more preferably 1) amino acid added, deleted, modified, and/or substituted, and is capable of retaining the binding affinity to PD-L1.

In another preferred embodiment, the light chain variable region further comprises human FR regions or mouse FR regions.

In another preferred embodiment, the light chain variable region has the amino acid sequence as shown in SEQ ID NO: 2.

In another preferred embodiment, the light chain variable region has the amino acid sequence as shown in SEQ ID NO: 9.

In a fourth aspect of the present invention, it provides a light chain of an antibody, which has the light chain variable region of the third aspect of the present invention.

In another preferred embodiment, the light chain of the antibody further comprises a light chain constant region.

In another preferred embodiment, the light chain constant region is of human, mouse or rabbit.

In a fifth aspect of the present invention, it provides an antibody, wherein the antibody comprises:

(1) the heavy chain variable region of the first aspect of the present invention; and/or
(2) the light chain variable region of the third aspect of the present invention; alternatively, the antibody has: the heavy chain of the second aspect of the present invention; and/or the light chain of the fourth aspect of the present invention.

In another preferred embodiment, the $EC_{50}$ of the affinity of the antibody to human PD-L1 protein (preferably wild type) is 30-80 ng/ml.

In another preferred embodiment, the $EC_{50}$ of the affinity of the antibody to human PD-L1 protein (preferably wild type) is 40-50 ng/ml.

In another preferred embodiment, the antibody is selected from the group consisting of an animal-derived antibody, a chimeric antibody, a humanized antibody, and a combination thereof.

In another preferred embodiment, the antibody is a double chain antibody or a single chain antibody.

In another preferred embodiment, the antibody is a monoclonal antibody.

In another preferred embodiment, the antibody is a partially or fully humanized monoclonal antibody.

In another preferred embodiment, the heavy chain variable region sequence of the antibody is shown in SEQ ID NO: 1 or 8; and/or the light chain variable region sequence of the antibody is shown in SEQ ID NO: 2 or 9.

In another preferred embodiment, the heavy chain variable region sequence of the antibody is shown in SEQ ID NO: 1; and the light chain variable region sequence of the antibody is shown in SEQ ID NO: 2.

In another preferred embodiment, the heavy chain variable region sequence of the antibody is shown in SEQ ID NO: 8; and the light chain variable region sequence of the antibody is shown in SEQ ID NO: 9.

In another preferred embodiment, the antibody is in the form of a drug conjugate.

In a sixth aspect of the present invention, it provides a recombinant protein which comprises:

(i) the heavy chain variable region of the first aspect of the present invention, the heavy chain of the second aspect of the present invention, the light chain variable region of the third aspect of the present invention, the light chain of the fourth aspect of the present invention, or the antibody of the fifth aspect of the present invention; and
(ii) an optional tag sequence that assists expression and/or purification.

In another preferred embodiment, the tag sequence comprises a 6His tag.

In another preferred embodiment, the recombinant protein (or polypeptide) comprises fusion protein.

In another preferred embodiment, the recombinant protein is a monomer, a dimer, or a multimer.

In a seventh aspect of the present invention, it provides a CAR construct, wherein the antigen binding domain of the CAR construct comprises a scFv that specifically binds to PD-L1, and the scFv has the heavy chain variable region of the first aspect of the present invention and the light chain variable region of the third aspect of the present invention.

In an eighth aspect of the present invention, it provides a recombinant immune cell expressing exogenous CAR construct of the seventh aspect of the present invention.

In another preferred embodiment, the immune cell is selected from the group consisting of: a NK cell, a T cell, a NKT cell, and a combination thereof.

In another preferred embodiment, the immune cell is derived from human or non-human mammals (such as mice).

In a ninth aspect of the present invention, it provides an antibody-drug conjugate comprising:

(A) an antibody moiety selected from the group consisting of: the heavy chain variable region of the first aspect of the present invention, the heavy chain of the second aspect of the present invention, the light chain variable region of the third aspect of the present invention, the light chain of the fourth aspect of the present invention, the antibody of the fifth aspect of the present invention, and a combination thereof; and (b) a coupling moiety coupled to the antibody moiety, and the coupling moiety is selected from the group consisting of a detectable label, a drug, a toxin, a cytokine, a radionuclide, an enzyme, and a combination thereof.

In another preferred embodiment, the antibody moiety is coupled to the coupling moiety via a chemical bond or linker.

In another preferred embodiment, the coupling moiety is selected from the group consisting of: a fluorescent or luminescent marker, a radioactive marker, MRI (magnetic resonance imaging) or CT (electronic computer X-ray tomography technique) contrast agent, or an enzyme capable of producing a detectable product, a radionuclide, a bio-toxin, a cytokine (such as IL-2, etc.), an antibody, an Fc fragment of an antibody, an scFv fragment of an antibody, a gold nanoparticle/nanorod, a viral particle, a liposome, a magnetic nanoparticle, a prodrug activating enzyme (such as DT-diaphorase (DTD) or biphenyl hydrolase-like protein (BPHL)), a chemotherapeutic agent (such as cisplatin) and any form of nanoparticles, and the like.

In a tenth aspect of the present invention, it provides use of an active ingredient selected from the group consisting of: the heavy chain variable region of the first aspect of the present invention, the heavy chain of the second aspect of the present invention, the light chain variable region of the third aspect of the present invention, the light chain of the fourth aspect of the present invention, the antibody of the fifth aspect of the present invention, the recombinant protein of the sixth aspect of the present invention, the immune cell of the eighth aspect, the antibody-drug conjugate of the ninth aspect of the present invention, and a combination thereof, wherein the active ingredient is used for
  (a) preparing a detection reagent or a kit;
  (b) preparing a drug or preparation for the prevention and/or treatment of PD-L1-related diseases; and/or
  (c) preparing a drug or preparation for the prevention and/or treatment of cancer or tumors.

In another preferred embodiment, the PD-L1-related disease is selected from the group consisting of tumors, inflammatory reactive diseases, and a combination thereof.

In another preferred embodiment, the drug or preparation is a PD-L1 inhibitor.

In another preferred embodiment, the tumor is selected from the group consisting of a hematological tumor, a solid tumor, and a combination thereof.

In another preferred embodiment, the tumor is selected from the group consisting of ovarian cancer, colon cancer, rectal cancer, melanoma (such as metastatic malignant melanoma), renal cancer, bladder cancer, breast cancer, liver cancer, lymphoma, hematological malignancies, head and neck cancer, glioma, gastric cancer, nasopharyngeal carcinoma, laryngeal carcinoma, uterine cancer, hysteroma, and osteosarcoma. Examples of other cancers that can be treated with the method of the invention comprise: bone cancer, pancreatic cancer, skin cancer, prostate cancer, skin or intraocular malignant melanoma, uterine cancer, cancer of the anal region, testicular cancer, carcinoma tubae, endometrial cancer, vaginal cancer, vulva cancer, Hodgkin's disease, non-Hodgkin's lymphoma, esophageal cancer, intestinal cancer, carcinoma of the endocrine system, thyroid cancer, parathyroid cancer, adrenal carcinoma, soft tissue sarcoma, urethral carcinoma, carcinoma of penis, chronic or acute leukemia comprising acute myeloid leukemia, chronic myeloid leukemia, acute lymphocyte leukemia, chronic lymphocyte leukemia, children's solid tumor, lymphocytic lymphoma, bladder cancer, carcinoma of the kidney or ureter, carcinoma of the renal pelvis, central nervous system (CNS) tumor, primary CNS lymphoma, tumor angiogenesis, spinal tumor, glioma of brain stem, pituitary adenoma, Kaposi's sarcoma, skin cancer, squamous-cell carcinoma, T cell lymphoma, environmentally induced cancer comprising asbestos-induced cancer, and combinations of the cancer.

In another preferred embodiment, the tumor is a tumor with high PD-L1 expression.

In another preferred embodiment, the drug or preparation is used for preparing a drug or preparation for the prevention and/or treatment of PD-L1-related (positive expression) diseases.

In another preferred embodiment, the antibody is in the form of a drug conjugate (ADC).

In another preferred embodiment, the detection reagent or kit is used for diagnosing PD-L1-related diseases.

In another preferred embodiment, the detection reagent or kit is used for detecting PD-L1 protein in a sample.

In another preferred embodiment, the detection reagent is a detecting strip.

In an eleventh aspect of the present invention, it provides a pharmaceutical composition comprising:
  (i) an active ingredient selected from the group consisting of: the heavy chain variable region of the first aspect of the present invention, the heavy chain of the second aspect of the present invention, the light chain variable region of the third aspect of the present invention, the light chain of the fourth aspect of the present invention, the antibody of the fifth aspect of the present invention, the recombinant protein of the sixth aspect of the present invention, the immune cell of the eighth aspect, the antibody-drug conjugate of the ninth aspect of the present invention, and a combination thereof; and
  (ii) a pharmaceutically acceptable carrier.

In another preferred embodiment, the pharmaceutical composition is a liquid formulation.

In another preferred embodiment, the pharmaceutical composition is an injection.

In another preferred embodiment, the pharmaceutical composition is used for inhibiting PD-L1, preferably for down-regulating or blocking the immunosuppressive effect of PD-L1.

In another preferred embodiment, the pharmaceutical composition is used for enhancing immunity, preferably for stimulating the activation, proliferation and cytokine secretion of immune cells (such as T cells).

In another preferred embodiment, the pharmaceutical composition is used for enhancing the immune response to tumors, preferably for enhancing the killing effect of immune cells on tumor cells.

In another preferred embodiment, the pharmaceutical composition is used for treating tumors.

In another preferred embodiment, the tumor is a tumor with high PD-L1 expression.

In another preferred embodiment, the pharmaceutical composition also comprises an additional anti-tumor agent.

In another preferred embodiment, the pharmaceutical composition is in a unit dosage form.

In another preferred embodiment, the anti-tumor agent comprises taxol, doxorubicin, cyclophosphamide, Axitinib, Lenvatinib or Pembrolizumab.

In another preferred embodiment, the anti-tumor agent can be individually present in a separate package with the antibody, or the anti-tumor agent can be coupled to the antibody.

In another preferred embodiment, the dosage form of the pharmaceutical composition comprises a dosage form for gastrointestinal administration or a dosage form for parenteral administration.

In another preferred embodiment, the dosage form for parenteral administration comprises intravenous injection, intravenous drip, subcutaneous injection, topical injection, muscle injection, intratumor injection, intraperitoneal injection, intracranial injection, or intra-cavity injection.

In a twelfth aspect of the present invention, it provides a polynucleotide encoding a polypeptide selected from the group consisting of:
  (i) the heavy chain variable region of the first aspect of the present invention, the heavy chain of the second aspect of the present invention, the light chain variable region of the third aspect of the present invention, the light chain of the fourth aspect of the present invention, or the antibody of the fifth aspect of the present invention; or (2) the recombinant protein of the sixth aspect of the present invention;

(3) the CAR construct of the seventh aspect of the present invention.

In a thirteenth aspect of the invention, it provides a vector comprising the polynucleotide of the twelfth aspect of the present invention.

In another preferred embodiment, the vector comprises: a bacterial plasmid, a phage, a yeast plasmid, a plant cell virus, a mammalian cell virus such as an adenovirus, retrovirus, or other vectors.

In a fourteenth aspect of the invention, it provides a genetically engineered host cell comprising the vector of the thirteenth aspect of the present invention or having the polynucleotide of the twelfth present aspect of the invention integrated into its genome.

In a fifteenth aspect of the present invention, it provides a method for in vitro detection (comprising diagnostic or non-diagnostic) of PD-L1 protein in a sample, wherein the method comprises the steps:

(1) contacting the sample with the antibody according to the fifth aspect of the present invention in vitro;

(2) detecting whether an antigen-antibody complex is formed, wherein the formation of the complex indicates the presence of PD-L1 protein in the sample.

In a sixteenth aspect of the present invention, it provides a detection plate comprising a substrate (or support plate) and a test strip, wherein the test strip comprising the antibody of the fifth aspect of the present invention or the immunoconjugate of the ninth aspect of the present invention.

In a seventeenth aspect of the present invention, it provides a kit, which comprises:

(1) a first container containing the antibody of the fifth aspect of the present invention; and/or (2) a second container containing a secondary antibody against the antibody of the fifth aspect of the present invention;

alternatively, the kit comprises the detection plate of the sixteenth aspect of the present invention.

In an eighteenth aspect of the present invention, it provides a method for preparing a recombinant polypeptide, which comprises the steps of:

(i) culturing the host cell of the fourteenth aspect of the present invention under a condition suitable for expression; and (b) isolating recombinant polypeptide from the culture, wherein the recombinant polypeptide is the antibody of the fifth aspect of the present invention or the recombinant protein of the sixth aspect of the present invention.

In a nineteenth aspect of the present invention, it provides a method for treating PD-L1-related diseases, wherein the method comprises: administering the antibody of the fifth aspect of the present invention, the antibody-drug conjugate of the antibody, or the CAR-T cell expressing the antibody, and a combination thereof, to a subject in need.

It should be understood that, in the present invention, each of the technical features specifically described above and below (such as those in the Examples) can be combined with each other, thereby constituting new or preferred technical solutions, which needs not be described one by one, due to space limitations.

MODES FOR CARRYING OUT THE PRESENT INVENTION

Figure 1:
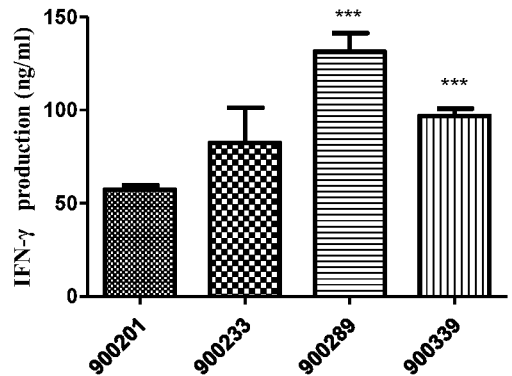
FIG. 1 shows the activation of PD-L1 antibody on PBMC.

Through extensive and intensive research, after extensive screening, the inventors unexpectedly obtained an anti-PD-L1 monoclonal antibody with extremely excellent affinity and specificity, and obtained a humanized antibody based on this antibody. The antibody of the present invention can bind to PD-L1 antigen with high specificity, which has high affinity and biological activity, and significantly inhibits the growth of cancerous tumors, especially tumors with high expression of PD-L1, but has no visible toxic and side effects on mammals themselves. The present invention has been completed on the basis of this.

Terms

In order to make the present invention easier to understand, some technical and scientific terms are specifically defined below. Unless clearly defined otherwise herein, all other technical and scientific terms used herein have meanings commonly understood by the ordinary skilled in the art to which the invention belongs.

The three-letter code and the mono-letter code of amino acids used in the present invention are described in J. Biol. Chem, 243, P3558 (1968).

As used herein, the term "administration" and "treatment" refer to applying an exogenous drug, therapeutic agent, diagnostic agent or composition to an animal, a human, a subject, a cell, a tissue, an organ, or biofluid. "Administration" and "treatment" can refer to treating, pharmacokinetics, diagnosis, research and experimental methods. The treatment of cells comprises contacts of reagents with cells, as well as contacts of reagents with fluids and contacts of fluids with cells. "Administration" and "treatment" also refer to in vitro and ex-vivo treatment by reagents, diagnosis, binding compositions or by another type of cells. When "treatment" is applied to human, animals or study subjects, it refers to therapeutic treatment, prevention or preventive measures, research and diagnosis, which comprises contacting the anti-human PD-L1 antibodies with people or animals, subjects, cells, tissues, physiological compartments or physiological fluid. As used herein, the term "treating" refers to the administration to a patient with a therapeutic agent for internal or external use, and the agent comprises any of the anti-human PD-L1 antibody and a composition thereof of the present invention, wherein the patient has one or more disease symptoms and the therapeutic agent is known to have a therapeutic effect on these symptoms. Typically, patients are administered in an amount (therapeutically effective amount) of therapeutic agent that is effective in relieving the symptoms of one or more diseases.

As used herein, the term "optional" or "optionally" means that the event or situation described later can occur but does not necessarily occur. For example, "optionally comprising 1-3 antibody heavy chain variable regions" means that there can be, but does not have to be, one, two, or three antibody heavy chain variable regions of a particular sequence.

The "sequence identity" of the present invention means that the degree of identity between two nucleic acids or two amino acid sequences in the presence of an appropriate mutation of substitution, insertion or deletion for optimal alignment and comparison. The sequence identity between the sequence of the present invention and a sequence with identity thereof may be at least 85%, 90%, or 95%, preferably at least 95%. Non-limiting examples include 85%, 86%, 87%, 88%, 89%, 90%, 91%, 92%, 93%, 94%, 95%, 96%, 97%, 98%, 99%, 100%.

As used herein, "conjugate (binder)" refers to a soluble receptor or fragment thereof or an analog thereof, or an antibody or fragment thereof or an analog thereof capable of binding to a target. As used in the present invention, "PD-L1 binder" refers to an antibody or a fragment thereof or an analog thereof that can specifically recognize PD-L1 and bind to PD-L1.

The term "PD-L1" generally refers to natural or recombinant human PD-L1, as well as non-human homologues of human PD-L1.

PD-L1

Programmed death 1 (PD-1) is a member of CD28 receptor family, which includes CD28, CTLA-4, ICOS, PD-1 and BTLA. The original members of this family, CD28 and ICOS, were discovered by enhanced function of T cell proliferation after adding monoclonal antibodies (Hutloff et al. (1999), Nature 397:263-266; Hansen et al. (1980), Immunogenics 10:247-260). Two cell surface glycoprotein ligands for PD-1 have been identified as PD-L1 and PD-L2, and they have been shown to down-regulate T cell activation and cytokine secretion after binding to PD-1 (Freeman et al. (2000), J Exp Med 192:1027-34; Latchman et al. (2001), Nat Immunol 2:261-8; Cater et al. (2002), Eur J Immunol 32:634-43; Ohigashi et al. (2000), Cl in Cancer Res 11:2947-53). PD-L1 (B7-H1) and PD-L2 (B7-DC) are both B7 homologues that bind to PD-1 but do not bind to other CD28 family members (Blank et al. 2004).

Expression of PD-L1 has been found in several human cancers, including human lung cancer, ovarian cancer, colon cancer, melanoma, and various myeloma (Iwai et al. (2002), PNAS 99:12293-7; Ohigashi et al. (2000, Cl in Cancer Res 11:2947-53). Previous results show that PD-L1, which is highly expressed in tumor cells, plays an important role in the immune escape of tumor by increasing the apoptosis of T cells. Researchers found that P815 tumor cell line transfected with PD-L1 gene can resist the lysis of specific CTL in vitro, and has stronger tumorigenicity and invasiveness after being inoculated into mice. These biological characteristics can be reversed by blocking PD-L1. Mice that knocked out the PD-1 gene and blocked the PD-L1/PD-1 pathway cannot form tumors when inoculated with tumor cells (Dong et al. (2002), Nat Med 8:793-800). It has also been suggested that PD-L1 may be associated with intestinal mucosal inflammation, and that inhibition of PD-L1 prevents atrophy associated with colitis (Kanai et al. (2003), JImmunol 171:4156-63). PD-1 is an immunosuppressive receptor first expressed on activated T cells and B cells. The interaction between the receptor and its ligand has always shown a weakened T cell response in vitro and in vivo. It has been shown that blocking the interaction between PD-1 and one of its ligands, PD-L1, improves the immunity of tumor-specific CD8$^+$ T cells, and therefore, can help the immune system remove tumor cells.

The PD-1/PD-L1 pathway is a well-established target for developing antibody therapies for cancer therapy. Anti-PD-1 antibodies can also be used for chronic viral infections. Memory CD8$^+$ T cells produced after acute viral infection have high function and constitute an important component of protective immunity. On the contrary, chronic infection is often characterized by different degrees of functional impairment (failure) of virus-specific T cell response, which is the main reason why the host cannot eliminate persistent pathogens.

Although functional effector T cells are initially produced in the early stage of infection, they gradually lose their function during chronic infection. Barber et al. (Barber et al., Nature 439:682-687 (2006)) showed that mice infected with the laboratory strain of LCMV developed chronic infection resulting in high levels of the virus in both blood and other tissues. These mice initially produced strong T cell responses, but eventually became infected as the depletion of T-cells. The authors found that the decrease in the number and function of effector T cells in chronically infected mice can be reversed by injecting antibodies that block the interaction between PD-1 and PD-L1.

Recently, studies have shown that PD-1 is highly expressed in T cells from HIV-infected individuals, and the receptor expression is associated with T cell dysfunction and disease progression (D-machi et al., Nature 443:350-4 (2006); Trautmann L. et al., Nat. Med. 12:1198-202 (2006)). In both studies, blocking the ligand PD-L1 significantly increased the proliferation of HIV-specific IFNγ-producing cells in vitro.

Antibody

As used herein, the term "antibody" refers to an immunoglobulin, which is a tetrapeptide chain structure composed of two identical heavy chains and two identical light chains connected by interchain disulfide bonds. The amino acid composition and sequence of the constant region of the immunoglobulin heavy chain vary, so the antigenicity varies. Accordingly, immunoglobulins can be divided into five classes, or isotypes of immunoglobulins, namely IgM, IgD, IgG, IgA and IgE, and their corresponding heavy chains are μ chain, δ chain, γ chain, α chain, and ε chain, respectively. Ig of the same class can be divided into different subclasses according to the difference in the amino acid compositions of the hinge regions and the numbers and positions of heavy chain disulfide bonds. For example, IgG can be divided into IgG1, IgG2, IgG3, and IgG4. Light chains are divided into κ chain and λ chain according to the difference of the constant regions. Each of the five types of Ig can comprise a κ chain or a λ chain. The subunit structures and three-dimensional configurations of different classes of immunoglobulins are well known to those skilled in the art. The antibody light chain of the present invention may further comprise a light chain constant region, which comprises a human or mouse κ, λ chain or a variant thereof.

In the present invention, the antibody heavy chain of the present invention may further comprise a heavy chain constant region, which comprises a human or mouse IgG1, IgG2, IgG3, IgG4 or a variant thereof. The sequence of about 110 amino acids near the N terminal of the antibody heavy chain or light chain varies greatly and is a variable region (Fv region); while the remaining amino acid sequence close to the C terminal is relatively stable and is a constant region. Variable regions comprise 3 hypervariable regions (HVR) and 4 framework regions (FR) with relatively conserved sequences. The 3 hypervariable regions determine the specificity of the antibody, also known as the complementarity determining regions (CDRs). Each light chain variable region (LCVR) and heavy chain variable region (HCVR) consists of 3 CDR regions and 4 FR regions, with an order from the amino terminal to the carboxyl terminal of: FR1, CDR1, FR2, CDR2, FR3, CDR3 and FR4. The 3 CDR regions of the light chain refer to LCDR1, LCDR2 and LCDR3; the 3 CDR regions of the heavy chain refer to HCDR1, HCDR2 and HCDR3.

The antibody of the present invention includes a murine antibody, a chimeric antibody, a humanized antibody, and preferably a humanized antibody. The term "murine antibody" in the present invention is an anti-PD-L1 monoclonal antibody prepared according to the knowledge and skills in the art. During preparation, the test subject was injected with the PD-L1 antigen, and then hybridomas expressing antibodies with the desired sequences or functional properties was isolated. In a preferred embodiment of the present invention, the murine PD-L1 antibody or antigen-binding fragment thereof may further comprise a light chain constant region of a murine κ, λ chain or a variant thereof, or further comprise a heavy chain constant region of murine IgG1, IgG2, IgG3 or a variant thereof.

The term "chimeric antibody" is an antibody formed by fusing the variable region of a murine antibody with the constant region of a human antibody, which can reduce the immune response induced by the murine antibody. Chimeric antibody is an antibody molecule expressed by myeloma tissue, wherein the myeloma tissue is transfected with a vector inserted a chimeric gene which is spliced by a V region gene of a murine antibody and a C region gene of a human antibody. It not only retains the high specificity and affinity of parent murine antibody, but also enables its human Fc segment to effectively mediate biological effect function.

The term "humanized antibody", also known as CDR-grafted antibody, refers to the antibodies produced by transplantation of mouse CDR sequences into the framework regions of human antibody variable regions, i.e., a different type of human germline antibody framework sequence. Humanized antibody is a modification of the variable region of the mouse antibody of the present invention, having a CDR region derived from (or substantially derived from) a non-human antibody (preferably a mouse monoclonal antibody), and FR regions and constant regions derived essentially from human-derived antibody sequences; that is, the CDR region sequences of mouse antibodies are grafted onto different types of human germline antibody framework sequences. Because CDR sequences are responsible for most antibody-antigen interactions, expression vectors can be constructed to express recombinant antibodies that mimic the properties of specific naturally occurring antibodies. Humanized antibodies can overcome the heterogeneous reaction induced by chimeric antibodies due to carrying a large amount of mouse protein components. Such framework sequences can be obtained from public DNA databases or published references that include germline antibody gene sequences. In order to avoid the decrease in activity resulting from the decrease of immunogenicity, the human antibody variable region framework sequence can be subjected to minimal reverse mutations or back mutations to maintain activity.

The term "antigen-binding fragment of an antibody" (or "antibody fragment" for short) refers to one or more fragments of an antibody that retain the ability to specifically bind to an antigen (for example, PD-L1). It has been shown that fragments of full-length antibodies can be used to perform the antigen-binding function of antibodies. Examples of the binding fragment included in the term "antigen-binding fragment of an antibody" include:

(i) an Fab fragment, which is a monovalent fragment consisting of VL, VH, CL and CHI domains;
  (ii) an F(ab')$_2$ fragment, which is a bivalent fragment comprising two Fab fragments connected by a disulfide bridge on the hinge region;
  (iii) an Fd fragment consisting of VH and CHI domains;
  (iv) an Fv fragment consisting of the VH and VL domains of one arm of an antibody.

An Fv antibody comprises a heavy chain variable region and a light chain variable region, but does not comprise a constant region, and is the smallest antibody fragment with all antigen binding sites. Generally, an Fv antibody also comprises a polypeptide linker between the VH and VL domain, and can form the structure required for antigen binding.

The term "antigenic determinant" of the present invention refers to a discrete three-dimensional site on an antigen that is recognized by an antibody or antigen-binding fragment of the present invention.

The term "CDR" refers to one of the 6 hypervariable regions within the variable domain of an antibody that mainly contributes to antigen binding. One of the most commonly used definitions of the 6 CDRs is provided by Kabat E. A et al., (1991) Sequences of proteins of immunological interest. NIH Publication 91-3242.

The term "epitope" or "antigenic determinant" refers to the site on an antigen where the immunoglobulin or the antibody specifically binds (for example, a specific site on the PD-L1 molecule). Epitope usually comprises at least 3, 4, 5, 6, 7, 8, 9, 10, 11, 12, 13, 14 or 15 consecutive or non-consecutive amino acids in a unique spatial conformation.

The terms "specific binding", "selective binding", "selectively bind", and "specifically bind", refer to the binding of an antibody to an epitope on a predetermined antigen. Generally, the antibody has an affinity (KD) that is approximately less than $10^{-7}$ M, such as approximately less than $10^{-8}$ M, $10^{-9}$ M or $10^{-10}$ M or less.

The term "competitive binding" means that the binding of an antibody to the same epitope (also called an antigenic determinant) on the extracellular region of PD-L1 or a part of the same epitope, which is recognized by the monoclonal antibody of the present invention. An antibody that binds to the same epitope as the monoclonal antibody of the present invention refers to an antibody that recognizes and binds to the amino acid sequence of PD-L1 recognized by the monoclonal antibody of the present invention.

The term "KD" or "Kd" refers to the dissociation equilibrium constant of a specific antibody-antigen interaction. Generally, the antibody of the present invention binds to PD-L1 with a dissociation equilibrium constant (KD) less than about $10^{-7}$ M, for example less than about $10^{-8}$ M, $10^{-9}$ M or $10^{-10}$ M or less, determined in a Biacore instrument using a surface plasmon resonance (SPR) technique.

As used herein, the term "antigenic determinant" refers to a discrete three-dimensional site on an antigen that is recognized by an antibody or antigen-binding fragment of the present invention.

The present invention includes not only an intact antibody, but also the fragments of the antibody having an immunological activity or a fusion protein formed by the antibody and another sequence. Therefore, the present invention also includes fragments, derivatives and analogs of the antibody.

In the present invention, antibodies include murine, chimeric, humanized or fully human antibodies prepared by techniques well known to those skilled in the art. Recombinant antibodies, such as chimeric and humanized monoclonal antibodies, including human and non-human parts, can be prepared using DNA recombinant techniques well known in the art.

As used herein, the term "monoclonal antibody" refers to an antibody secreted by a clone derived from a single cell.

Monoclonal antibodies are highly specific and direct against a single epitope. The cells may be eukaryotic, prokaryotic or phage cloned cell lines.

In the present invention, the antibody may be monospecific, bispecific, trispecific, or multispecific.

In the present invention, the antibody of the present invention further includes a conservative variant thereof, which refers to a polypeptide formed by substitution of at most 10, preferably at most 8, more preferably at most 5, and most preferably at most 3 amino acids with amino acids having similar or analogous property, as compared to the amino acid sequence of the antibody of the present invention. These conservative variant polypeptides are preferably formed by carrying out the amino acid substitution according to Table A.

TABLE A

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Human PD-L1 Specific Antibody

The present invention provides an anti-human PD-L1 antibody (hereinafter referred to as PD-L1 antibody). More specifically, the present invention provides an antibody with high specificity and high affinity against PD-L1, which comprises a heavy chain and a light chain, wherein the heavy chain contains a heavy chain variable region (VH) amino acid sequence, and the light chain contains a light chain variable region (VL) amino acid sequence.

Preferably, the respective CDRs of the heavy chain variable region (VH) amino acid sequence and the light chain variable region (VL) amino acid sequence are selected from the group consisting of:
- a1) SEQ ID NO: 3;
- a2) SEQ ID NO: 4;
- a3) SEQ ID NO: 5;
- a4) SEQ ID NO: 6;
- a5) GIS;
- a6) SEQ ID NO: 7;
- a7) a sequence with PD-L1 binding affinity which is obtained through addition, deletion, modification and/or substitution of at least one amino acid (e.g., 1-5, 1-3, preferably 1-2, more preferably 1) of any amino acid sequence of the above amino acid sequences.

In another preferred embodiment, the sequence obtained through addition, deletion, modification and/or substitution of at least one amino acid is preferably an amino acid sequence having a homology of at least 80%, preferably at least 85%, and more preferably at least 90%, most preferably at least 95%.

The antibody of the present invention may be a double-chain or single-chain antibody, and may be selected from animal-derived antibodies, chimeric antibodies and humanized antibodies, more preferably be selected from humanized antibodies and human-animal chimeric antibodies, more preferably a fully humanized antibody.

The antibody derivative of the present invention may be a single-chain antibody, and/or an antibody fragment, for example, Fab, Fab', (Fab') 2 or other antibody derivatives known in the art, etc., and may be any one or more of IgA, IgD, IgE, IgG and IgM antibodies or other subtype antibodies.

In the present invention, the animal is preferably a mammal, such as mouse.

The antibody of the present invention may be a murine antibody, a chimeric antibody, a humanized antibody, a CDR grafted and/or modified antibody that targets human PD-L1.

In a preferred embodiment of the present invention, any one or several sequences of SEQ ID NOs 3, 4 and 5, or sequences thereof that are obtained through addition, deletion, modification and/or substitution of at least one amino acid and have PD-L1 binding affinity, are located in the CDRs of heavy chain variable region (VH).

In a preferred embodiment of the present invention, any one or several sequences of SEQ ID NO: 6, amino acid sequence of GIS, and SEQ ID NO: 7, or sequences thereof that are obtained through addition, deletion, modification and/or substitution of at least one amino acid and have PD-L1 binding affinity, are located in the CDRs of light chain variable region (VL).

In a more preferred embodiment of the present invention, VH CDR1, CDR2 and CDR3 are independently selected from any one or several sequences of SEQ ID NOs 3, 4 and 5, or sequences thereof that are obtained through addition, deletion, modification and/or substitution of at least one amino acid and have PD-L1 binding affinity; VL CDR1, CDR2 and CDR3 are independently selected from any one or several sequences of SEQ ID NO: 6, amino acid sequence of GIS, and SEQ ID NO: 7, or sequences thereof that are obtained through addition, deletion, modification and/or substitution of at least one amino acid and have PD-L1 binding affinity.

In above content of the present invention, the number of the added, deleted, modified and/or substituted amino acids, preferably is no more than 40%, more preferably no more than 35%, more preferably 1-33%, more preferably 5-30%, more preferably 10-25%, and is more preferably no more than 15-20% of the total number of the amino acids of the initial amino acid sequence.

In the present invention, the number of addition, deletion, modification and/or substitution of amino acids is generally 1, 2, 3, 4 or 5, preferably 1-3, more preferably 1-2, and most preferably 1.

According to some embodiments of the present invention, it provides a PD-L1 antibody, and the antibody heavy chain variable region thereof further comprises a heavy chain FR region of murine IgG1, IgG2, IgG3, IgG4 or variants thereof. In some embodiments, the sequence of antibody heavy chain variable region is: SEQ ID NO: 1 or 8. Further, the PD-L1 antibody comprises a heavy chain constant region of murine IgG1, IgG2, IgG3, IgG4 or variants thereof.

According to some embodiments of the present invention, it provides a PD-L1 antibody, and the antibody light chain variable region thereof further comprises a light chain FR region of murine κ, λ chain or variants thereof. In some embodiments, the sequence of antibody light chain variable region is SEQ ID NO: 2 or 9. Further, the PD-L1 antibody comprises a light chain constant region of murine κ, λ chain or variants thereof. Further, the PD-L1 antibody comprises a light chain constant region of human κ, λ chain or variants thereof.

In another preferred embodiment, the amino acid sequence of the heavy chain variable region is as shown in SEQ ID NO: 1 or 8, wherein the double underscores are the amino acid sequences of CDR1, CDR2, and CDR3 of the heavy chain variable region in turn.

(SEQ ID NO: 1)
QVQLQQSGAELVKPGASVKLSCKAS<u>GYAFTGYTI</u>HWVKQRSGLGLEWLG

<u>WFYPGSGTLKYNEKFKD</u>KATLTADKSSSTVYLELSRLTSEDSAVYFCAR

<u>HGTGTLMAMDY</u>WGQGTSVTVSS (SEQ ID NO: 8)
QVQLVQSGAEVKKPGASVKVSCKAS<u>GYAFTGYTI</u>HWVRQAPGQRLEWMG

<u>WFYPGSGTLKYSEKFQG</u>RVTITRDKSLSTAYMELSSLRSEDTAVYYCAR

<u>HGTGTLMAMDY</u>WGQGTLVTVSS

In another preferred embodiment, the amino acid sequence of the light chain variable light is as shown in SEQ ID NO: 2 or 9, wherein the double underscores are the amino acid sequences of CDR1', CDR2', and CDR3' of the light chain variable region in turn.

(SEQ ID NO: 2)
DVVVTQTPLSLPVSFGDQVSISCRSS<u>QSLANSYGNTYLS</u>WYLHKPGQSP

QLLIY<u>GISNRFS</u>GVPDRFSGSGSGTDFTLKISTIKPEDLGMYYC<u>LQGTH</u>

<u>QPPT</u>FGGGTKLEIK (SEQ ID NO: 9)
DVVMTQTPLSLSVTPGQPASISCKSS<u>QSLANSYGNTYLS</u>WYLHKPGQSP

QLLIY<u>GISNRFS</u>GVPDRFSGSGSGTDFTLKISRVEAEDVGVYYC<u>LQGTH</u>

<u>QPPT</u>FGQGTKLEIK

Antibody Preparation

Any method suitable for producing monoclonal antibodies can be used to produce the PD-L1 antibodies of the present invention. For example, an animal can be immunized with a linked or naturally occurring PD-L1 protein or fragment thereof. Suitable immunization methods can be used, including adjuvants, immunostimulants, repeated booster immunizations, and one or more approaches can be used.

Any suitable form of PD-L1 can be used as an immunogen (antigen) to produce non-human antibodies specific for PD-L1 and to screen the biological activity of the antibody. The immunogen can be used alone or in combination with one or more immunogenicity enhancers known in the art. The immunogen can be purified from natural sources or produced in genetically modified cells. DNA encoding an immunogen may be of genomic origin or non-genomic origin (e.g. cDNA). Appropriate genetic vectors can be used to express the DNA encoding the immunogen, including but not limited to adenovirus vectors, baculovirus vectors, plasmids and non-viral vectors.

An exemplary method for producing the PD-L1 antibody of the present invention is described in Example 1.

Humanized antibodies can be selected from any kind of immunoglobulin, including IgM, IgD, IgG, IgA and IgE. In the present invention, the antibody is an IgG antibody, and the IgG1 subtype is used. Screening of antibodies with the biological assays described in the examples below makes it easy to optimize the necessary constant domain sequences to produce the desired biological activity.

Likewise, any type of light chain can be used in the compounds and methods herein. Specifically, the κ, λ chain or variants thereof can be used in the compounds and methods of the present invention.

An exemplary method of humanizing the PD-L1 antibody of the present invention is described in Example 2.

The present invention provides use and method of the PD-L1 binding molecule, the nucleic acid molecule, the host cell, the immunoconjugate and the pharmaceutical composition of the present invention in preventing and/or treating diseases related to PD-L1. The diseases related to PD-L1 that can be prevented and/or treated with the PD-L1 binding molecule of the present invention are described in detail below.

The polynucleotides encoding the mature polypeptides of the present invention comprise coding sequences encoding only the mature polypeptide; coding sequences of the mature polypeptide and various additional coding sequences; coding sequences (and optionally additional coding sequences) of the mature polypeptide, and non-coding sequences.

The term "polynucleotide encoding a polypeptide" may include a polynucleotide that encodes the polypeptide, or a polynucleotide that also includes additional coding and/or non-coding sequences.

The present invention also relates to polynucleotides that hybridize to the sequences as described above and having at least 50%, preferably at least 70%, more preferably at least 80% identical between the two sequences. In particular, the present invention relates to polynucleotides that can hybridize to the polynucleotides of the present invention under stringent conditions. In the present invention, "stringent conditions" means: (1) hybridization and elution at lower ionic strength and higher temperature, such as 0.2×SSC, 0.1% SDS, 60° C.; or (2) hybridization when adding a denaturant, such as 50% (v/v) formamide, 0.1% calf serum/0.1% Ficoll, 42° C., or the like; or (3) hybridization only occurs when the identity between the two sequences is at least 90% or more, more preferably 95% or more. And the polypeptide encoded by the hybridizable polynucleotide has the same biological function and activity as the mature polypeptide shown in SEQ ID NO: 1, SEQ ID NO: 2, SEQ ID NO: 8 and/or SEQ ID NO: 9.

The whole length of the nucleotide sequence or the fragment thereof of the antibody of the present invention can be obtained via PCR amplification, recombinant method or artificial synthesis. One feasible method is to synthesize relevant sequences by artificial method, especially when the fragment is short in length. Usually, several small fragments are synthesized first, and then they are linked together to obtain a fragment with a long sequence. In addition, the sequence coding the light chain and heavy chain and the expression label (e.g. 6His) can be fused together to form a fusion protein.

Once a relevant sequence is obtained, the relevant sequence can be obtained in large quantities using a recombination method. This is usually carried out by cloning the sequence into a vector, transforming a cell with the vector, and then separating the relevant sequence from the proliferated host cell by conventional methods.

In addition, a relevant sequence can be synthesized artificially, especially when the fragment is short in length. Usually, several small fragments are synthesized first, and then are linked together to obtain a fragment with a long sequence. The DNA sequence can then be introduced into a variety of existing DNA molecules (or, for example, vectors) and cells known in the art.

The term "nucleic acid molecule" refers to a DNA molecule and an RNA molecule. The nucleic acid molecule can be single-stranded or double-stranded, but is preferably double-stranded DNA. When a nucleic acid is placed in a functional relationship with another nucleic acid sequence, the nucleic acids are "effectively linked". For example, if a promoter or enhancer affects the transcription of a coding sequence, the promoter or enhancer is effectively linked to the coding sequence.

The term "vector" refers to a nucleic acid molecule capable of transporting another nucleic acid to which it has been linked. In one embodiment, the vector is "a plasmid", which refers to a circular double-stranded DNA loop into which additional DNA segments can be ligated.

The present invention further relates to a vector comprising the suitable DNA sequence and a suitable promoter or a control sequence as discussed above. These vectors can be used to transform suitable host cells to enable them to express protein.

The term "host cell" refers to a cell into which an expression vector has been introduced. The host cell can be a prokaryotic cell, such as a bacterial cell; or a lower eukaryotic cell, such as a yeast cell; or a higher eukaryotic cell, such as a plant cell or an animal cell (such as a mammalian cell).

The step of transforming host cells with recombinant DNA as described in the present invention can be carried out by techniques well known in the art. The obtained transformant can be cultured by conventional methods, and the transformant expresses the polypeptide encoded by the gene of the present invention. According to the host cell used, it is cultured in a conventional medium under suitable conditions.

At present, a DNA sequence encoding the protein of the present invention (or fragments thereof, or derivatives thereof) can completely be obtained by chemical synthesis. The DNA sequence can then be introduced into a variety of existing DNA molecules (or, for example, vectors) and cells known in the art. In addition, mutations can also be introduced into the protein sequences of the present invention by chemical synthesis.

The present invention further relates to a vector comprising the suitable DNA sequence and a suitable promoter or a control sequence as discussed above. These vectors can be used to transform suitable host cells to enable them to express protein.

The host cell can be a prokaryotic cell, such as a bacterial cell; or a lower eukaryotic cell, such as a yeast cell; or a higher eukaryotic cell, such as a mammalian cell. Representative examples are: *Escherichia coli, Streptomyces*; Bacterial cells of *Salmonella typhimurium*; Fungal cells such as yeast; insect cells of *Drosophila* S2 or Sf9; animal cells of CHO, COS 7, 293 cell, etc.

Transformation of host cells with recombinant DNA can be carried out using conventional techniques well known to the skilled in the art. When the host is a prokaryote such as *E. coli*, competent cells capable of absorbing DNA can be harvested after the exponential growth phase and treated with $CaCl_2$), the steps used are well known in the art. Another method is to use $MgCl_2$. If necessary, the transformation can also be carried out by means of electroporation. When the host is a eukaryote, the following DNA transfection methods can be used: calcium phosphate coprecipitation method, conventional mechanical method, such as microinjection, electroporation, liposome packaging, etc.

The obtained transformants can be cultured by a conventional method to express a polypeptide encoded by a gene of the present invention. According to the host cell used, the medium used in the culture may be selected from a variety of conventional media. And the host cell can be cultured under conditions suitable for the growth of the host cell. After the host cell has grown to an appropriate cell density, the selected promoter is induced by a suitable method (such as temperature conversion or chemical induction) and the cells are cultured for a further period of time.

The recombinant polypeptide in the method above may be expressed in the cells or on the cell membrane, or secreted out of the cell. If necessary, the recombinant protein can be separated and purified by various separation methods according to its physical, chemical, and other properties. These methods are well known to those skilled in the art.

The examples of the method include, but are not limited to, conventional renaturation treatment, treatment by protein precipitant (such as salt precipitation), centrifugation, cell lysis by osmosis, sonication, super centrifugation, molecular sieve chromatography (gel chromatography), adsorption chromatography, ion exchange chromatography, high performance liquid chromatography (HPLC), and any other liquid chromatography, and the combination thereof.

The monoclonal antibody obtained can be identified by conventional means. For example, the binding specificity of a monoclonal antibody can be determined by immunoprecipitation or an in vitro binding assay (such as radioimmunoassay (RIA) or enzyme-linked immunosorbent assay (ELISA)).

The antibodies of the present invention may be used alone, or may be bound or coupled to detectable markers (for diagnostic purposes), therapeutic agents, PK (protein kinase) modified moieties, or any combination of these substances.

Detectable markers for diagnostic purposes include, but are not limited to, fluorescent or luminescent markers, radiological markers, MRI (magnetic resonance imaging) or CT (electronic computer X-ray tomography technique) contrast agents, or enzymes capable of producing detectable products.

Couplable therapeutic agents include, but are not limited to, insulin, IL-2, interferon, calcitonin, GHRH peptides, intestinal peptide analogues, albumin, antibody fragments, cytokines, and hormones.

In addition, therapeutic agents that can bind or couple to antibodies of the present invention include, but are not limited to: 1. radionuclides; 2. biotoxins; 3. cytokines such as IL-2 and that like; 4. gold nanoparticle/nanorods; 5. virus particle; 6. liposome; 7. magnetic nanoparticle; 8. prodrug activating enzymes; 10. chemotherapeutic agents (e.g., cisplatin) or nanoparticles in any form, etc.

Pharmaceutical Composition

The invention further provides a composition. In the preferred examples, the composition is a pharmaceutical composition comprising the antibody, or an active fragment, a fusion protein or an ADC thereof, or a corresponding CAR-T cell, and a pharmaceutically acceptable carrier. In general, these substances may be formulated in a non-toxic, inert and pharmaceutically acceptable aqueous carrier medium, wherein the pH is generally about 5-8, preferably, pH is about 6-8, though the pH value may be varied depending on the nature of the substances to be formulated and the condition to be treated. The formulated pharmaceutical composition may be administered by conventional routes, including (but not limited to): intratumoral, intraperitoneal, intravenous, or topical administration.

The antibody of the present invention can also be used for cell therapy by expressing the nucleotide sequence in a cell, for example, the antibody is used for chimeric antigen receptor T cell immunotherapy (CAR-T) and the like.

The pharmaceutical composition of the present invention can be directly used for binding to a PD-L1 protein molecule, and thus can be used for preventing and treating diseases related to PD-L1. In addition, other therapeutic agents can also be used simultaneously.

The pharmaceutical composition according to the present invention comprises a safe and effective amount (e.g. 0.001-99 wt %, preferably 0.01-90 wt %, preferably 0.1-80 wt %) of the monoclonal antibody according to the present invention (or a conjugate thereof) and a pharmaceutically acceptable carrier or excipient. Such carriers include, but are not limited to, saline, buffer, glucose, water, glycerin, ethanol and the combination thereof. The pharmaceutical preparation should be matched to the method of administration. The pharmaceutical composition of the present invention can be prepared in the form of injection, for example, prepared by a conventional method using physiological saline or an aqueous solution containing glucose and other adjuvants. Pharmaceutical compositions such as injections and solutions are preferably prepared under sterile conditions. The dosage of active ingredient is therapeutically effective amount, for example from about 1 microgram per kilogram body weight to about 5 milligrams per kilogram body weight per day. Further, the polypeptide of the present invention can also be used in combination with the other therapeutic agents.

When a pharmaceutical composition is used, a safe and effective amount of pharmaceutical composition is administered to a mammal, wherein the safe and effective amount is usually at least about 10 mg/kg of body weight, and in most cases does not exceed about 50 mg/kg body weight, preferably the dose is about 10 mg/kg body weight to about 20 mg/kg body weight. Of course, the particular dose should also depend on various factors, such as the route of administration, patient healthy status, which are well within the skills of an experienced physician.

Use for Detection and Kit

The antibody of the present invention can be used for detection, for example, for detecting samples, thereby providing diagnostic information.

In the present invention, the samples (specimens) used include cells, tissue samples and biopsy specimens. The term "biopsy" used in the present invention shall include all kinds of biopsy known to those skilled in the art. Therefore, the biopsy used in the present invention may include, for example, tissue samples prepared by endoscopic methods or organ puncture or needle biopsy.

The samples used in the present invention include fixed or preserved cell or tissue samples.

The present invention also provides a kit comprising the antibody (or fragment thereof) of the present invention. In a preferred embodiment of the present invention, the kit further includes a container, an instruction for use, buffer, and the like. In a preferred embodiment, the antibody of the present invention can be immobilized on a detection plate.

Cancer

Blocking PD-L1 by PD-L1 binding molecule of the invention can enhance the immune response to cancerous cells in the patient. PD-L1 is abundant in a variety of human cancers (Dong et al. (2002) Nat Med 8:787-9). The interaction between PD-1 and PD-L1 results in a decrease in tumor infiltrating lymphocytes, a decrease in T-cell receptor mediated proliferation, and immune evasion by the cancerous cells. CN 106397592A Page 16/31 of the specification (Dong et al. (2003) J Mol Med 81:281-7; Konishi et al. (2004) Clin. Cancer Res.10:5094-5100). Immune suppression can be reversed by inhibiting the local interaction of PDL1 to PD-1 and the effect is additive when the interaction of PD-L2 to PD-1 is blocked as well (Iwai et al. (2002) PNAS 99:12293-7; Brown et al. (2003) J. Immunol. 170: 1257-66). A PD-L1 binding molecule of the invention may be used alone to inhibit the growth of cancerous tumors. Alternatively, a PD-L1 binding molecule of the invention may be used in conjunction with other immunogenic agents, standard cancer treatments, or other antibodies, as described below.

Accordingly, in one embodiment, the invention provides a method of preventing and/or treating cancer in a subject, comprising administering to the subject a therapeutically effective amount of PD-L1 binding molecule of the invention so as to inhibit growth of tumor cells in the subject.

Preferred cancers which can be prevented and/or treated using the PD-L1 binding molecule of the invention include cancers typically responsive to immunotherapy. Non-limiting examples of preferred cancers for treatment include lung cancer, ovarian cancer, colon cancer, rectal cancer, melanoma (e.g., metastatic malignant melanoma), renal cancer, bladder cancer, breast cancer, liver cancer, lymphoma, hematological malignancy, head and neck cancer, glioma, gastric cancer, nasopharyngeal cancer, laryngeal cancer, cervical cancer, corpus carcinoma, osteosarcoma. Examples of other cancers that may be treated using the methods of the invention include bone cancer, pancreatic cancer, prostatic cancer, skin cancer, cancer of the head or neck, cutaneous or intraocular malignant melanoma, uterine cancer, cancer of the anal region, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) Int. Immunol. 17:133-144).

Optionally, PD-L1 binding molecule of the invention can be combined with an immunogenic agent, such as cancerous cells, purified tumor antigens (including recombinant proteins, peptides, and carbohydrate molecules), and cells transfected with genes encoding immune stimulating cytokines (He et al. (2004) J. Immunol. 173:4919-28). Non-limiting examples of immunogenic agent that can be used include peptides of melanoma antigens, such as peptides of gp100, MAGE antigens, Trp-2, MARTI and/or tyrosinase, or tumor cells transfected to express the cytokine GM-CSF.

In humans, some tumors have been shown to be immunogenic such as melanomas. It is anticipated that the tumor responses in the host can be activated by blocking PD-L1 by the PD-L1 binding molecule of the invention to promote T cell activation. PD-L1 blockade (such as PD-L1 antibody, e.g., the PD-L1 binding molecule of the invention) is likely to be the most effective when combined with a tumor vaccination protocol. Many experimental strategies for vaccination against tumors have been devised (see Rosenberg, S., 2000, Development of Cancer Vaccines, ASCO Educational Book Spring: 60-62; Logothetis, C, 2000, ASCO Educational Book Spring: 300-302; Khayat, D. 2000, ASCO Educational Book Spring: 414-428; Foon, K. 2000, ASCO Educational Book Spring: 730-738; et al.). In one of these strategies, a vaccine is prepared using autologous or allogeneic tumor cells. These cellular vaccines have been shown to be the most effective when the tumor cells are transduced to express GM-CSF. GM-CSF has been shown to be a potent activator of antigen presentation for tumor vaccination (Dranoff et al. (1993) Proc. Nat 1. Acad. Sci U.S.A. 90:3539-43).

The study of gene expression and large scale gene expression patterns in various tumors has led to the definition of so-called tumor specific antigens (Rosenberg, SA (1999) Immunity 10:281-7). In many cases, these tumor specific antigens are differentiation antigens expressed in the tumors and in the cells from which the tumors arose, for example gp100, MAGE antigens, and Trp-2. More importantly, many of these antigens can be shown to be the targets of tumor specific T cells found in the host. PD-L1 binding molecule of the invention may be used in combination with tumor-specific proteins and/or peptides produced by recombination to generate an immune response to these proteins. These proteins are normally viewed by the immune system as self-antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266:2011-2013). Tumor antigens may also be "neo-antigens" expressed in cancer cells because of somatic mutations that alter protein sequence or create fusion proteins between two unrelated sequences (e.g. bcr-abl in the Philadelphia chromosome).

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PDL1 blockade (such as PDL1 antibody, e.g., PD-L1 binding molecule of the invention) is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269:1585-1588; Tamura, Y. et al. (1997) Science 278:117-120).

Dendritic cells (DCs) are potent antigen presenting cells that can be used to elicit antigen-specific responses. DCs can be produced ex vivo and loaded with various protein and peptide antigens as well as tumor cell extracts (Nestle, F. et al. (1998) Nature Medicine 4:328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with PD-L1 blockade (such as PD-L1 antibody, e.g., PD-L1 binding molecule of the invention) to activate more potent anti-tumor responses.

CAR-T (Chimeric Antigen Receptor T-Cell Immunotherapy) is another cell therapy for treating malignant tumors. Chimeric Antigen Receptor T-Cell (CAR-T cells) are T cells from a patient that have been genetically infected with a chimeric protein of an antigen-binding moiety of an antibody against certain tumor antigen coupled with CD3-ζ chain or intracellular portion of FcεPIγ for expressing a chimeric antigen receptor (CAR). Meanwhile, co-stimulating signaling sequence may be introduced for increasing cytotoxic activity, proliferation and survival of T cells, and promoting the release of cytokines. After reprogramming, T cells from the patient expanded in vitro to produce a large number tumor-specific CAR-T cells which are then transfused back into the patient for treating tumor. PD-L1 blocking agents (such as PD-L1 antibodies, e.g., the PD-L1 binding molecule of the invention) may be used in combination with CAR-T cell therapy for activating stronger anti-tumor responses.

PD-L1 binding molecule of the invention may also be combined with standard cancer treatments. PD-L1 binding molecule of the invention may be effectively combined with chemotherapeutic regimens. In these instances, it may be possible to reduce the dose of chemotherapeutic reagent administered (Mokyr, M. et al. (1998) Cancer Research 58:5301-5304). An example of such a combination is an anti-PD-L1 antibody in combination with decarbazine for the treatment of melanoma. Another example of such a combination is an anti-PD-L1 antibody in combination with interleukin-2 (IL-2) for the treatment of melanoma. The scientific rationale behind the combined use of PD-L1 binding molecule of the invention and chemotherapy is that cell death, which is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 binding molecule of the invention. Inhibition of angiogenesis leads to tumor cell death which may provide tumor antigens to the host antigen presentation pathways.

The PD-L1 binding molecule of the invention can also be used in combination with antibody against other tumor-specific antigen. The antibody against other tumor-specific antigen includes but not limited to anti-EGFR antibody, anti-EGFR variant antibody, anti-VEGFa antibody, anti-HER2 antibody, or anti-CMET antibody. Preferably, the antibody is a monoclonal antibody.

PD-L1 binding molecule of the invention can also be used in combination with bispecific antibodies that target Fc alpha or Fc gamma receptor-expressing effectors cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell aspect of these responses would be enhanced by the use of PD-L1 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of immunosuppressive proteins which are expressed by the tumors. Particularly, these include TGF-β (KehrL. et al. (1986) Exp. Med. 163:1037-1050), IL-10 (Howard, M. & Garra, A. (1992) Immunology Today 13:198-200), and Fas ligand (Hahne, M. et al. (1996) Science 274:1363-1365). Each of these antibodies among these may be used in combination with PD-L1 binding molecule of the invention to counteract the effects of the immunosuppressive agent and favor tumor immune responses by the host.

Other antibodies which may be used to activate host immune responsiveness can be used in combination with anti-PD-L1. Anti-CD40 antibodies are able to substitute effectively for T cell helper activity (Ridge. et al (1998) Nature 393:474-478) and can be used in combination with PD-L1 binding molecule of the invention. Activating antibodies to T cell costimulatory molecules such as OX-40 and ICOS, as well as antibodies which block the activity of negative costimulatory molecules such as CTLA-4 may also be provided for increased levels of T cell activation.

Bone marrow transplantation is currently being used to treat a variety of tumors of hematopoietic origin. While graft versus host disease is a consequence of this treatment, therapeutic benefit may be obtained from graft-versus-tumor responses. PD-L1 blockade can be used to increase the effectiveness of the tumor specific T cells. There are also several experimental treatment protocols that involve ex vivo activation and expansion of antigen specific T cells and adoptive transfer of these cells into recipients in order to use antigen-specific T cells against tumor. These methods may also be used to activate T cell responses to infectious agents such as CMV. Ex vivo activation in the presence of PD-L1 binding molecule of the invention may be expected to increase the frequency and activity of the adoptively transferred T cells. Therefore, the invention also provides a method for activating immune cells (such as PBMC or T cells) ex vivo, including contacting the immune cells with the PD-L1 binding molecule of the invention.

Infectious Diseases

Other methods of the invention are used to treat patients that have been exposed to particular toxins or pathogens. Accordingly, another aspect of the invention provides a method of preventing and/or treating an infectious disease in a subject comprising administering to the subject a PD-L1 binding molecule of the invention, such that the subject is prevented and/or treated for the infectious disease.

Similar to the application for tumors as discussed above, PD-L1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HTV, Hepatitis (A, B, & C), Influenza, Herpes, Giardia, Malaria, *Leishmania, Staphylococcus aureus, Pseudomonas Aeruginosa*. PD-L1 blockade is particularly useful against established infections by agents such as HIV that present altered antigens over the course of the infections. These novel epitopes are recognized as foreign at the time of anti-human PD-L1 administration, thus provoking a strong T cell response that is not affected by negative signals through PD-L1.

Some examples of pathogenic viruses causing infections treatable by the methods of the invention include HIV, hepatitis (A, B, or C), herpes virus (e.g., VZV, HSV-L HAV-6, HSV-II, and CMV, EB virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include *chlamydia*, rickettsial bacteria, mycobacteria, staphylococci, streptococci, pneumococci, meningococci and gonococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Autoimmune Reactions

Anti-PDL1 antibodies may provoke and amplify autoimmune responses. Therefore, it is possible to consider using anti-PD-L1 blockade in combination with various self-proteins in order to devise vaccination protocols to efficiently generate immune responses against these self-proteins for disease treatment.

Chronic Inflammatory Diseases

Anti-PD-L1 antibodies may also be used to treat diseases such as chronic inflammatory diseases, such as lichen planus, a T-cell mediated chronic inflammatory mucocutaneous disease. Accordingly, in another aspect the invention provides a method of abrogating chronic inflammatory disease by T cells, comprising administering to the subject a PD-L1 binding molecule of the invention. The invention provides anti-PD-L1 antibody and its use in the treatment of ocular diseases and autoimmune diseases. The diseases include but are not limited to psoriasis, psoriatic arthritis, ankylosing spondylitis, multiple sclerosis, inflammatory bowel diseases (e.g. Crohn's disease, ulcerative colitis, etc.), osteoarthritis, rheumatoid arthritis (RA), rheumatic arthritis or osteoporosis, inflammatory fibrosis (e.g. scleroderma, pulmonary fibrosis and sclerosis), asthma (including allergic asthma), allergies, and cancer.

The Main Advantages of the Invention (a) The antibody of the present invention has excellent biological activity and specificity.
(b) The humanized antibody of the present invention has lower immunogenicity while retain comparable affinity to PD-L1 as compared with murine antibodies and chimeric antibodies.
(c) Blocking of PD-L1 by the antibody of the present invention can significantly enhance the immune response to cancer cells in a patient.
(d) The antibody of the present invention has an affinity to PD-L1 of certain non-human mammals (e. g. monkeys) comparable to that of human PD-L1, facilitates testing in animal models and quality control assay.
(e) By relieving the inhibition of PD-L1 on the activity of immune cells (such as T cells), the antibody can effectively activate the activity of antigen-specific T cells, significantly enhance the anti-tumor effect of T cells, and stimulate the secretion of human IFN-γ and IL-2 more effectively, thus improving the immune system response of patients to tumors and achieving the purpose of killing tumor cells.

The present invention will be further illustrated below with reference to the specific examples. It is to be understood that these examples are for illustrative purposes only and are not intended to limit the scope of the invention. For the experimental methods in the following examples, in which the specific conditions are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified. Unless indicated otherwise, parts and percentage are weight parts and weight percentage.

Experiments without specific conditions specified in the examples or test cases of the present invention are usually carried out under conventional conditions or according to the conditions suggested by the raw material/commodity manufacturer. Reagents that do not indicate specific sources are conventional reagents purchased from the market.

EXAMPLE 1

Preparation Method of Mouse Monoclonal Antibody Against Human PD-L1

The method for preparing murine monoclonal antibodies uses the hybridoma preparation technique invented by Kohler and Milstein in 1975 (Nature, 1975, 256:495-497). At first, human PD-L1-His protein (Sino biological, #10084-H08H) was emulsify with Freund's adjuvant, and then 5 mice of each strain of BALB/c, CD1, C57BL/6, and SJL were subjected to multi-spot subcutaneous immunization. After three rounds of immunization, serum was taken to detect the titer by ELISA. After the titer reached the predetermined standard, spleen cells were taken and fused with SP2/0 myeloma cells. Hybridoma polyclonal cells were screened by HAT, then polyclonal cell lines that specifically bind to human PD-L1 were screened using ELISA and monocloned. The specifically bound monoclonal cell lines were screened again using ELISA method, and the binding capacity with monkey PD-L1 was detected. ES-2 cells were used for FACS screening, and the screened monoclonal cell lines were screened for affinity (SPR). Finally, monoclonal hybridoma cells 36C06/D8 expressing human PD-L1 antibody were obtained. The screening data are listed in Table 1.

TABLE 1

Hybridoma screening data

| Clone Number | Polyclone OD value (human) | Polyclone OD value (monkey) | Monoclone OD value (human) | Monoclone OD value (monkey) | Monoclone FACS | Monoclone KD (M) |
|---|---|---|---|---|---|---|
| 36C06-D8 | 1.269 | 1.077 | 1.386 | 0.6685 | 99697 | 2.74E-09 |
| 2C12-F2 | 1.845 | 1.488 | 1.886 | 1.131 | 76175 | 2.53E-09 |
| 3C12-H10 | 2.325 | 1.630 | 2.108 | 1.938 | 88596 | 5.73E-11 |
| 3F08-G12 | 1.909 | 1.151 | 2.113 | 1.761 | 30400.5 | 4.46E-09 |
| 42-C02-F9 | 2.597 | 2.509 | 2.702 | 2.768 | 5229.5 | 6.73E-09 |
| 45-G11-E4 | 2.148 | 2.667 | 2.174 | 2.619 | 4621.5 | 4.27E-09 |
| 40-H10-B7 | 2.351 | 2.655 | 2.16 | 2.65 | 4681.5 | 7.40E-09 |
| 13H11-E7 | 1.927 | 1.776 | 2.428 | 1.791 | 79521 | 3.92E-10 |
| 9H05-C4 | 1.954 | 1.958 | 2.087 | 1.887 | 34077.5 | 4.47E-09 |
| 6G05-D4 | 1.586 | 1.987 | 1.855 | 1.397 | 78737 | 2.40E-09 |

As can be seen from Table 1, after screening, among many hybridomas, hybridoma 36C06/D8 (or the antibody produced by it) has high binding activity with human PD-L1 protein and monkey PD-L1 protein, and has the highest affinity activity at the cell binding level.

EXAMPLE 2

Clone and Humanization of V-Gene Sequence of the Anti-PD-L1 Antibody

2.1 Clone of cDNA Sequences of Immunoglobulin from Hybridoma Cells

The DNA sequence encoding the variable region of mouse antibody expressed by hybridoma 36C06/D8 was determined by using the principle of Baobio 5'RACE technology. In brief, SMART 5'RACE synthesis kit (TAKARA, #634859) was used to prepare specific cDNAs of heavy chain and light chain genes according to the manufacturer's instructions. PCR products were analyzed by agarose gel electrophoresis. The expected amplification sizes of the variable regions of both heavy and light chains are about 500 base pairs. The amplified PCR product with appropriate band size obtained by the reaction was cloned into the vector pEASY-Blunt Simple vector (Beijing TransGen, #CB111-02) and transformed into Stellar *Escherichia coli* competent cells (TAKARA, #636763). Clones were screened by colony PCR using common M13 forward or reverse primers, and 2-3 clones were selected from each reaction for DNA sequencing analysis. The results of each sequencing reaction for each clone were analyzed using Expasy-Translate tool (Http://web.expasy.org/translate/). Sequencing results showed that the V region sequence of anti-PD-L1 antibody expressed by 36C06/D8 was as follows:

900289-VH

SEQ ID NO: 1

QVQLQQSGAELVKPGASVKLSCKAS<u>GYAFTGYTI</u>HWVKQRSGLGLEWLG

W<u>FYPGSGTL</u>KYNEKFKDKATLTADKSSSTVYLELSRLTSEDSAVYFC<u>AR</u>

<u>HGTGTLMAMDY</u>WGQGTSVTVSS

900289-VL

SEQ ID NO: 2

DVVVTQTPLSLPVSFGDQVSISCRSS<u>QSLANSYGNTY</u>LSWYLHKPGQSP

QLLIY<u>GIS</u>NRFSGVPDRFSGSGSGTDFTLKISTIKPEDLGMYYC<u>LQGTH</u>

<u>QPPT</u>FGGGTKLEIK

Wherein, the underlined regions are CDRs (definited by IMGT, and listed separately as follows):

TABLE 2

CDR sequence of murine anti-PD-L1 antibody

| Domain | | sequence | SEQ ID NO |
|---|---|---|---|
| VH | CDR1 | GYAFTGYT | 3 |
| | CDR2 | FYPGSGTL | 4 |
| | CDR3 | ARHGTGTLMAMDY | 5 |
| VL | CDR1 | QSLANSYGNTY | 6 |
| | CDR2 | GIS | — |
| | CDR3 | LQGTHQPPT | 7 |

2.2 Construction and Expression of Chimeric 900289 Antibody

The chimeric heavy chain and light chain were constructed by linking the cDNA cloned by PCR of mouse 36C06/D8 VH and VL regions with human IgG1 and κ constant region, respectively. The 5' and 3' ends of the mouse cDNA sequence were modified with PCR primers designed to add appropriate leading sequences to each strand and to add restriction sites enabling cloning into the existing recombinant antibody expression vector pHB-Fc. The pHB-Fc plasmid vector was prepared as follows: the pcDNA/HA-FLAG (Accession #FJ524378) vector was used as the starting plasmid, and the constant region sequence of human IgG1 or K was added after the endonuclease EcoRI, the human cytomegalovirus (HCMV) promoter sequence (Accession #X17403) was added before the endonuclease HindIII, and the Chinese hamster glutamine synthetase gene (Accession X03495) was added before the HCMV promoter after the ampicillin tolerance gene.

The host cells used for protein expression were CHO—S cells (Thermophilia #R80007). CHO—S cells were transfected with a liposome complex obtained by mixing the vector expressing heavy and light chain of chimeric antibody with polyetherimide (PEI). The cells were put into an incubator and cultured for 3-5 days. The antibody concentration from supernatant of transfected CHO—S was measured by indirect ELISA. It is shown that the transfected CHO—S cells secrete about 60 mg/L of chimeric IgG1-K antibody (hereinafter also referred to as 900289).

2.3 Humanization of Murine Anti-Human PD-L1 Antibody-Preparation Method of Humanized Antibody The humanization of antibodies adopted the following methods. The variable region sequence of the antibody was compared with the available sequence in NCBI protein database. The human framework region suitable for constructing heavy chain and light chain of CDR transplantation was finally determined through identification and analysis.

During the modification, according to the conserved amino acid residues in the FR region of human antibody and the important amino acid residues in the FR region of the antibody, the modification sites were designed, and the variable regions of the heavy and light chains of the chimeric antibody were designed with humanized mutation respectively. The PCR technology was used to amplify and construct humanized point mutation antibody expression plasmids. The humanized point mutation antibody expression plasmids were expressed in CHO—S cells and purified to obtain humanized antibody proteins. Using ELISA, receptor binding inhibition assay, and Biacore and cell activity detection, a humanized PD-L1 monoclonal antibody (hereinafter also called 900339) with excellent performance was obtained. The VH and VL sequences of the obtained humanized PD-L1 antibody are shown in SEQ ID NOs: 8 and 9, respectively:

900339-VH

SEQ ID NO: 8

QVQLVQSGAEVKKPGASVKVSCKAS<u>GYAFTGYTI</u>HWVRQAPGQRLEWMG

W<u>FYPGSGTLKYSEKFQG</u>RVTITRDKSLSTAYMELSSLRSEDTAVYYCAR

<u>HGTGTLMAMDY</u>WGQGTLVTVSS

900339-VL

SEQ ID NO: 9

DVVMTQTPLSLSVTPGQPASISCKSS<u>QSLANSYGNTYLS</u>WYLHKPGQSP

QLLIY<u>GISNRFS</u>GVPDRFSGSGSGTDFTLKISRVEAEDVGVYYC<u>LQGTH</u>

<u>QPPT</u>FGQGTKLEIK

EXAMPLE 3

Identification of the Function of Chimeric Antibody and Humanized Antibody

3.1 Binding Specificity Test of PD-L1 Antibody to PD-L1 Protein from Different Species (ELISA)

3.1.1 Binding Activity Test of Chimeric Antibody 900289, Humanized Antibody 900339 and Control huIgG1 (900201) to Human PD-L1 Protein Specifically, 1 µg/ml huPD-L1-his protein (purchased from Sino Biological, #10084-H08H) was added to the ELISA plate at 50 ul/well, and coated at 2-8° C. for more than 12 hours. The raffinate of plate coating was discarded, 200 ul of 3% milk was added to each well, and blocked at room temperature for 1 hour. PBST not less than 200 uL was added to each well for washing once. The antibody sample to be tested was diluted to 100 µg/ml, then diluted 5 times for 11 gradients, and added to the ELISA plate at 100 µL/well. After incubation at room temperature for 1 hour, PBST no less than 200 uL was added to each well. After washing for 4 times, HRP-conjugated Rabbit Anti-Human IgG Fc Antibody (Luoyang Baiaotong Experimental Material Center, #C030222) diluted 25000 times with 3% milk-PBST was added as 100 µL/well. After incubating at room temperature for 1 hour, PBST not less than 200 µL was added to each well, washed 6 times and beat dry. 100 µL of TMB Substrate was added to each well. After 5 minutes of reaction at room temperature, 50 µL/well of 2 M $H_2SO_4$ was added to terminate the reaction. The ELISA plate with stopped reaction was placed on the microplate reader, and the absorbance of OD450 value was read at 450 nm wavelength.

The results (see Table 3) show that both chimeric antibody 900289 and humanized antibody 900339 have good binding ability to human PD-L1 protein.

TABLE 3

Binding activity of anti-PD-L1 antibody to human PD-L1

| Antibody to be tested | $EC_{50}$ (ug/ml) |
|---|---|
| 900201 | NA |
| 900289 | 0.04326 |
| 900339 | 0.04851 |

Note:
NA indicates no binding activity

3.1.2 Binding Activity Test of Chimeric Antibody 900289, Humanized Antibody 900339 and Control huIgG1 to Monkey or Mouse PD-L1 Protein The experimental method is similar to that of human PD-L1 binding experiment. The huPD-L1-his in the test example was replaced with rhPD-L1-his protein (Sino Biological, #90251-C08H) or moPD-L1-his protein (Sino Biological, #50010-M8H), and other steps are the same.

The results (see Table 4) show that chimeric antibody 900289 and humanized antibody 900339 bind to monkey PD-L1 protein, but do not bind to mouse PD-L1 protein or the binding ability is very weak.

TABLE 4

Binding activity of anti-PD-L1 antibody to monkey or mouse PD-L1

| Antibody to be tested | $EC_{50}$ (ug/ml) | |
|---|---|---|
| | rhPD-L1 | moPD-L1 |
| 900201 | NA | NA |
| 900289 | 0.1399 | NA |
| 900339 | 0.1151 | NA |

Note:
NA indicates no binding activity

3.2 Affinity Assay of Chimeric Antibody and Humanized Antibody to Human PD-L1 (Biacore)

In this experiment, SPR method was used to determine antibody-antigen binding kinetics and affinity.

Anti-Human Capture-CM5 chip (GE, #BR-1005-30) was prepared according to the coupling method of Human Antibody Capture Kit (GE, #BR-1008-39) and Amino Coupling Kit (GE, BR-1000-50). The chip was balanced at room temperature for 20-30 min, and loaded into a Biacore 8K instrument. B5D1 was diluted to the experimental working concentration with equilibration buffer. The antigen was diluted to 50 nM with equilibration buffer, then diluted 3 times for 7 concentration gradients, and 2 zero concentrations (i.e. equilibration buffer) and 1 repeated concentration (generally is a repeat of lowest concentration) were set. In the order of antibody, antigen huPD-L1 (Sino Biological, #10084-H08H), and regeneration, 10 antigen concentrations (2 zero concentrations, 7 gradient concentrations, and 1 repeat concentration) were cyclically subjected to experimental analysis. The antigen injection flow rate was 30 uL/min, the binding time was 120 seconds, and the dissociation time was 600 seconds. After the analysis was completed, the corresponding analysis program was selected to analyze the data to confirm that there is no obvious reference binding. Kinetics, 1:1 binding model was selected to fit the data, and the kinetic related parameters of Ka, Kd and KD values of human-mouse chimeric antibody and humanized antibody were obtained (Table 5).

The results show that humanized antibody 900339 and chimeric antibody 900289 both have strong affinity, and the binding ability of them was at the same level.

TABLE 5

Affinity test results of human-mouse chimeric antibody and human recombinant B7H1

| Name | Ka (1/Ms) | Kd (1/s) | KD (M) |
|---|---|---|---|
| 900289 | 2.33E+05 | 3.12E−04 | 1.34E−09 |
| 900339 | 2.33E+05 | 2.19E−04 | 9.40E−10 |

3.3 Test for Blocking the Binding of PD-L1 Antigen to PD-1 Molecule by PD-L1 Antibody (Competition Method)

The antigen huPD-L1-moFc (800023, Huabo Bio) was diluted to 15 ug/ml with PBS solution containing 1% BSA (1% BSA/PBS), added into a 96-well U-shaped plate as 20 uL per well, and mixed with serially diluted anti-PD-L1 antibody at a volume ratio of 1:1. The reaction was carried out at room temperature for 15 min, and simultaneously set negative control (only added 1% BSA/PBS) and positive control (only added PD-L1-moFc). The suspension of cells (3C2-huPD-1-6F4, Huabo Bio) expressing human PD-1 in the logarithmic growth phase was centrifuged (1000 rpm×5 min) to discard the culture medium, and the cells were resuspended with 1% BSA/PBS to a living cell density of 1×10$^6$/ml. 20 uL (2×10$^4$ cells) per well was added to a 96-well U-shaped plate pre-incubated with PD-L1-moFc and anti-PD-L1 antibody, and reacted at room temperature for 15 min. The reacted 96-well U-shaped plate was resuspended with 1% BSA/PBS, centrifuged (300 g×3 min) to discard the supernatant, and washed like this for twice. Alexa488-goat anti-mouse-Fc (Jackson ImmunoResearch, #115-545-071) diluted at 1:300 was added, and reacted at room temperature for 15 min away from light. The reacted 96-well U-shaped plate was resuspended with 1% BSA/PBS, centrifuged (300 g×3 min) to discard the supernatant, and washed like this for three times. Finally, the plate was resuspended with 100 µL of 1% BSA/PBS for each well and the fluorescence intensity of the first channel was detected by flow cytometry (BD, #Accuri C6).

The results (see Table 6) show that both chimeric antibody 900289 and humanized antibody 900339 have significant blocking effect on human PD-L1/PD-1, and the blocking force is equivalent.

TABLE 6

Blocking activity of PD-L1 antibody

| Antibody to be tested | huPD-L1-moFc/ huPD-1 binding IC$_{50}$ (ng/ml) | huPD-L1-moFc/ huB7.1 binding IC$_{50}$ (ng/ml) |
|---|---|---|
| 900201 | NA | NA |
| 900289 | 1.995 | NA |
| 900339 | 2.424 | NA |

Note:
NA indicates no blocking activity

3.4 Nonspecific Binding Test (SPR) for Identification of Chimeric Antibody and Humanized Antibody In this experiment, SPR method was used to determine the nonspecific adsorption effect between antibody and non-target molecules.

The chip of Series S Sensor Chip CM5 (GE, #BR-1005-30) was balanced at room temperature for 20-30 min, and loaded into Biacore 8K (GE) instrument. Lysozyme solution from eggs (Sigma, #L3790) and trypsin inhibitor 1-S type from soybean (Sigma, #T-2327) were immobilized respectively to the CM5 chip using Amino Coupling Kit (GE, #BR-1000-50). The injection buffer was HBS-EP (1×) (GE, #BR-1006-69), and 4 balance cycles were set. Polyclonal rabbit anti-lysozyme (ABcam, Ab391), anti-trypsin inhibitor antibody (LifeSpan Biosciences, #LS-C76609), chimeric antibody and humanized antibody were diluted to 1000 nM with equilibration buffer. The flow rate was set as 5 uL/min, injection channels were 1, 2 and 3, and flow cells were 1 and 2. The binding time was 10 min and the dissociation time was 15 min. The regeneration flow rate was 50 uL/min, and 0.85% phosphoric acid solution (ProteOn, 176-2260) was used for regeneration for 60s, and then 50 mM sodium hydroxide solution was used for regeneration for 30s.

The results show (see Table 7) that chimeric antibody 900289 and humanized antibody 900339 have no obvious nonspecific electrostatic and hydrophobic binding.

TABLE 7

Test results of non-specific adsorption of antibody and non-target molecule

| Cycle | Name | Lysozyme (RU) | Trypsin inhibitor (RU) | Deactivated carboxymethyl glucan (RU) | Carboxymethyl glucan (RU) |
|---|---|---|---|---|---|
| 4 | Buffer | 0 | −1.9 | 2.5 | 0.6 |
| 5 | Anti-lysozyme polyclonal antibody | 7477.4 | 22.7 | 34.8 | 20.5 |
| 6 | Anti-trypsin inhibitor | 23.4 | 9594 | 23.9 | 18.1 |
| 8 | 900339 | 9.2 | 11.5 | 10.9 | 9.4 |
| 10 | 900289 | 1.8 | 0 | 2.4 | −2.5 |
| 11 | Anti-lysozyme polyclonal antibody | 6735.1 | 30.3 | 38.1 | 25.5 |

TABLE 7-continued

Test results of non-specific adsorption of antibody and non-target molecule

| Cycle | Name | Lysozyme (RU) | Trypsin inhibitor (RU) | Deactivated carboxymethyl glucan (RU) | Carboxymethyl glucan (RU) |
|---|---|---|---|---|---|
| 12 | Anti-trypsin inhibitor | 41.3 | 9286 | 35.9 | 29 |

Note:
The interaction below 20RU is weak and can be ignored;
if the value exceeds 20RU, it is considered as an obvious interaction;
if the value exceeds 100RU, it is considered as a strong interaction.

3.5 Activation of PBMC by Chimeric Antibody and Humanized Antibody 1 ug/ml of antibody to be tested and 1 ug/ml of anti-human CD3 antibody (BioLegend, #300314) were coated jointly into a 96-well cell culture plate as 200 µL/well, and coated at 2-8° C. overnight. The next day, the coating liquid was discarded, the plate was washed twice with PBS, and then the residual liquid in the well was sucked dry with a pipette. The PBMC was diluted with medium to a living cell density of $5\times10^5$/mL, 200 uL per well ($1\times10^5$ cells/well), added to a pre-coated 96-well cell culture plate, and cultured under the condition of 37° C., 5% $CO_2$ for 5 days. After completion of culture, the 96-well cell culture plate was centrifuged at 300 g×10 min, and the secretion amount of human IFN-γ in the upper cell culture medium was detected by Human IFN-γ ELISA MAX™ Standard Kit (BioLegend, #430101).

The result is shown in FIG. 1. The addition of chimeric antibody 900289 or human antibody 900339 stimulated the secretion of cytokine IFN-γ more effectively than the negative control 900201.

3.6 the Activation of Chimeric Antibody and Humanized Antibody on T Cells was Determined in Mixed Lymphatic Reaction Monocytes were isolated from PBMC using the EasySep™ Human Monocyte Enrichment Kit without CD16 Depletion Kit (STEMCELL™, #19058) and cultured according to the ImmunoCult™ Dendritic Cell Culture Kit (STEMCELL™, #10985) to harvest mature dendritic cells for later use. $CD4^+$ T lymphocytes were isolated from another individual-derived PBMC using the EasySep™ Human $CD4^+$ T cell enrichment kit (STEMCELL™, #19052). The mature dendritic cells were resuspended with culture medium into a cell suspension with a living cell density of $2\times10^5$/mL of cell suspension. 50 uL ($1\times10^4$ cells/well) of the suspension was added to each well of a 96 well cell culture plate. At the same time, $CD4^+$ T lymphocytes were resuspended with culture medium into a cell suspension with a living cell density of $2\times10^6$/mL. 50 uL ($1\times10^5$ cells/well) of the suspension was added to each well of the 96-well cell culture plate containing dendritic cells and mixed well to obtain a MLR reaction system. Anti-PD-L1 antibody with a final concentration of 1 ug/ml was added into the MLR system, fully mixed and cultured under the condition of 37° C., 5% $CO_2$ for 5 days. At the end of the culture, the 96-well cell culture plate was centrifuged at 300 g×10 min. The secretion amounts of human IFN-γ and IL-2 in the upper cell culture medium were detected by Human IFN-γ ELISA MAXIM Standard Kit (BioLegend, #430101) and Human IL-2 ELISA MAX™ Standard Kit (BioLegend, #431801), respectively.

Figure 2:
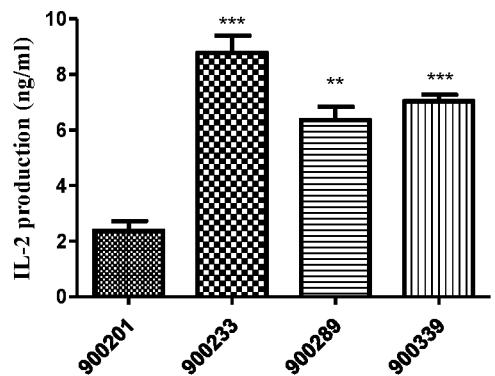
FIG. 2 shows the activation effect of PD-L1 antibody on CD4+ T cells in MLR system, and the secretion amount of IL-2 in upper cell culture.
Figure 3:
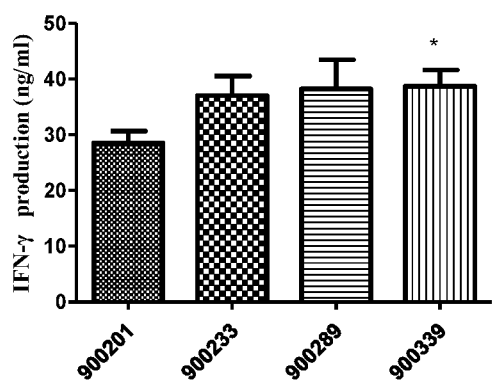
FIG. 3 shows the activation effect of PD-L1 antibody on CD4+ T cells in MLR system, and the secretion amount of IFN-γ in upper cell culture.

The results are shown in FIGS. 2 and 3, 900233 in the figure is Roche humanized PD-L1 antibody as a positive control, which was cloned according to the humanized sequence provided in patent US20160319022, and transiently transfected for expression. The results show that chimeric antibody 900289 and humanized antibody 900339 are more effective in stimulating human IFN-γ and IL-2 secretion than the negative control 900201.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. An antibody specific against PD-L1, wherein the antibody comprises:
    (1) a heavy chain variable region comprising the following three complementary determining regions (CDRs):
    CDR1 as shown in SEQ ID NO: 3,
    CDR2 as shown in SEQ ID NO: 4, and
    CDR3 as shown in SEQ ID NO: 5; and
    (2) a light chain variable region comprising the following three complementarity determining regions (CDRs):
    CDR1' as shown in SEQ ID NO: 6,
    CDR2', wherein the amino acid sequence of CDR2' is GIS, and
    CDR3' as shown in SEQ ID NO: 7.

2. The antibody of claim 1, wherein the antibody is selected from the group consisting of a murine antibody, a chimeric antibody, and a humanized antibody.

3. The antibody of claim 1, wherein the heavy chain variable region sequence of the antibody is as shown in SEQ ID NO: 1, and the light chain variable region sequence of the antibody is as shown in SEQ ID NO: 2 or
    wherein the heavy chain variable region sequence of the antibody is as shown in SEQ ID NO: 8, and the light chain variable region sequence of the antibody is as shown in SEQ ID NO: 9.

4. A recombinant protein which comprises:
    (i) the antibody of claim 1; and
    (ii) an optional tag sequence that assists expression and/or purification.

5. A CAR construct, wherein the antigen binding domain of the CAR construct comprises a scFv that specifically binds to PD-L1, and the scFv has a heavy chain variable region comprising the following three complementary determining regions (CDRs):
    CDR1 as shown in SEQ ID NO: 3,
    CDR2 as shown in SEQ ID NO: 4, and
    CDR3 as shown in SEQ ID NO: 5; and
    a light chain variable region comprising the following three complementarity determining regions (CDRs):
    CDR1' as shown in SEQ ID NO: 6,
    CDR2', wherein the amino acid sequence of CDR2' is GIS, and
    CDR3' as shown in SEQ ID NO: 7.

6. The antibody of claim 1, wherein the heavy chain variable region sequence of the antibody is as shown in SEQ ID NO: 1; and
    the light chain variable region sequence of the antibody is as shown in SEQ ID NO: 2.

7. The antibody of claim 1, wherein the heavy chain variable region sequence of the antibody is as shown in SEQ ID NO: 8; and
    the light chain variable region sequence of the antibody is as shown in SEQ ID NO: 9.

8. A method for treating PD-L1-related diseases, wherein the method comprises: administering the antibody of claim 1 to a subject in need, wherein the PD-L1-related diseases comprise tumors with positive PD-L1 expression.

9. A method for in vitro detection of PD-L1 protein in a sample, wherein the method comprises the steps:
    (1) contacting the sample with the antibody of claim 1 in vitro;
    (2) detecting whether an antigen-antibody complex is formed, wherein the formation of the complex indicates the presence of PD-L1 protein in the sample.

10. A pharmaceutical composition comprising:
    (i) an active ingredient, which is the antibody of claim 1; and
    (ii) a pharmaceutically acceptable carrier.

* * * * *